(12) United States Patent
Traubenberg et al.

(10) Patent No.: US 9,539,351 B2
(45) Date of Patent: Jan. 10, 2017

(54) RADIATION SOURCE MODULE AND FLUID TREATMENT SYSTEM

(75) Inventors: George Traubenberg, London (CA); Douglas Penhale, London (CA)

(73) Assignee: Trojan Technologies, London (CA)

( * ) Notice: Subject to any disclaimer, the term of this patent is extended or adjusted under 35 U.S.C. 154(b) by 99 days.

(21) Appl. No.: 13/994,941

(22) PCT Filed: Dec. 13, 2011

(86) PCT No.: PCT/CA2011/001350
§ 371 (c)(1),
(2), (4) Date: Sep. 3, 2013

(87) PCT Pub. No.: WO2012/079149
PCT Pub. Date: Jun. 21, 2012

(65) Prior Publication Data
US 2013/0334438 A1    Dec. 19, 2013

Related U.S. Application Data

(60) Provisional application No. 61/457,048, filed on Dec. 16, 2010.

(51) Int. Cl.
*A61L 2/10* (2006.01)
*C02F 1/32* (2006.01)

(52) U.S. Cl.
CPC .............. *A61L 2/10* (2013.01); *C02F 1/325* (2013.01); *C02F 2201/324* (2013.01);
(Continued)

(58) Field of Classification Search
CPC .............. C02F 1/00; C02F 1/32; C02F 1/325; C02F 2201/32; C02F 2201/322; C02F 2201/3225; C02F 2201/3227; C02F 2201/3228; A61L 2/08; A61L 2/10
(Continued)

(56) References Cited

U.S. PATENT DOCUMENTS

| 4,482,809 A | 11/1984 | Maarschalkerweerd |
| 4,872,980 A | 10/1989 | Maarschalkerweerd |

(Continued)

FOREIGN PATENT DOCUMENTS

| CN | 1481337 A | 3/2004 |
| CN | 1662454 A | 8/2005 |

(Continued)

OTHER PUBLICATIONS

International Search Report for International Application No. PCT/CA2011/001350 with a mailing date of Apr. 26, 2012.

(Continued)

*Primary Examiner* — David E Smith
(74) *Attorney, Agent, or Firm* — Katten Muchin Rosenman LLP

(57) ABSTRACT

There is described a radiation source module for use in a fluid treatment system. The radiation source module comprises: a housing having an inlet, an outlet and a fluid treatment zone disposed between. The fluid treatment zone comprises a first wall surface and a second wall surface interconnected by a floor surface. The first wall surface, the second wall surface and the floor surface are configured to receive a flow of fluid through the fluid treatment zone. The radiation source module further comprises at least one radiation source assembly secured with respect to the first wall surface and the second wall surface and a module motive coupling element connected to the housing and configured to be coupled to a module motive element to permit the radiation source module to be installed in and extracted from the fluid treatment system. A fluid treatment system comprising the radiation source module is also described.

25 Claims, 21 Drawing Sheets

(52) U.S. Cl.
CPC ..... *C02F 2201/328* (2013.01); *C02F 2201/3225* (2013.01); *C02F 2201/3227* (2013.01)

(58) Field of Classification Search
USPC ....... 250/428, 431, 432 R, 435–438, 455.11; 210/748.1, 748.11, 748.13
See application file for complete search history.

(56) References Cited

U.S. PATENT DOCUMENTS

| | | | |
|---|---|---|---|
| 5,006,244 A | | 4/1991 | Maarschalkerweerd |
| 5,208,461 A | * | 5/1993 | Tipton .......................... 250/436 |
| 5,368,826 A | * | 11/1994 | Weltz ........................ A61L 2/10 |
| | | | 210/748.11 |
| 5,418,370 A | | 5/1995 | Maarschalkerweerd |
| 5,503,800 A | * | 4/1996 | Free ................................. 422/24 |
| 5,504,335 A | | 4/1996 | Maarschalkerweerd |
| 5,539,210 A | | 7/1996 | Maarschalkerweerd |
| 5,952,663 A | * | 9/1999 | Blatchley, III ......... B01J 19/123 |
| | | | 250/435 |
| RE36,896 E | | 10/2000 | Maarschalkerweerd |
| 6,500,346 B1 | | 12/2002 | Taghipour et al. |
| 2002/0113021 A1 | * | 8/2002 | Traubenberg ........... C02F 1/325 |
| | | | 210/232 |
| 2004/0069954 A1 | * | 4/2004 | Traubenberg .......... B01J 19/123 |
| | | | 250/436 |
| 2005/0232825 A1 | * | 10/2005 | Fowler et al. ................ 422/121 |

FOREIGN PATENT DOCUMENTS

| | | |
|---|---|---|
| CN | 101248511 A | 8/2008 |
| WO | 2004/000735 A1 | 12/2003 |
| WO | 2008/055344 A1 | 5/2008 |

OTHER PUBLICATIONS

First Office Action for Chinese Patent Application No. 2011800605583 with a date of notification of Jun. 6, 2014.
Second Office Action for Chinese Patent Application No. 201180060558.3 with a date of notification of Apr. 3, 2015.

\* cited by examiner

RADIATION SOURCE MODULE AND FLUID TREATMENT SYSTEM

CROSS-REFERENCE TO RELATED APPLICATION

The present application claims the benefit under 35 U.S.C. §119(e) of provisional patent application Ser. No. 61/457,048, filed Dec. 16, 2010, the contents of which are hereby incorporated by reference.

BACKGROUND OF THE INVENTION

Field of the Invention

In one of its aspects the present invention relates to a radiation source module for use in a fluid treatment system. In another of its aspects, the present invention relates to a fluid treatment system incorporating a radiation source module.

Description of the Prior Art

Fluid treatment systems are generally known in the art. More particularly, ultraviolet (UV) radiation fluid treatment systems are generally known in the art.

Early treatment systems comprised a fully enclosed chamber design containing one or more radiation (preferably UV) lamps. Certain problems existed with these earlier designs. These problems were manifested particularly when applied to large open flow treatment systems which are typical of larger scale municipal waste water or potable water treatment plants. Thus, these types of reactors had associated with them the following problems:

relatively high capital cost of reactor;
difficult accessibility to submerged reactor and/or wetted equipment (lamps, sleeve cleaners, etc);
difficulties associated with removal of fouling materials from fluid treatment equipment;
relatively low fluid disinfection efficiency, and/or
full redundancy of equipment was required for maintenance of wetted components (sleeves, lamps and the like).

The shortcomings in conventional closed reactors led to the development of the so-called "open channel" reactors.

For example, U.S. Pat. Nos. 4,482,809, 4,872,980 and 5,006,244 (all in the name of Maarschalkerweerd and all assigned to the assignee of the present invention and hereinafter referred to as the Maarschalkerweerd #1 patents) all describe gravity fed fluid treatment systems which employ ultraviolet (UV) radiation.

Such systems include an array of UV lamp modules (e.g., frames) which include several UV lamps each of which are mounted within sleeves which extend between and are supported by a pair of legs which are attached to a crosspiece. The so-supported sleeves (containing the UV lamps) are immersed into a fluid to be treated which is then irradiated as required. The amount of radiation to which the fluid is exposed is determined by the proximity of the fluid to the lamps, the output wattage of the lamps and the flow rate of the fluid past the lamps. Typically, one or more UV sensors may be employed to monitor the UV output of the lamps and the fluid level is typically controlled, to some extent, downstream of the treatment device by means of level gates or the like.

The Maarschalkerweerd #1 patents teach fluid treatment systems which were characterized by improved ability to extract the equipment from a wetted or submerged state without the need for full equipment redundancy. These designs compartmentalized the lamp arrays into rows and/or columns and were characterized by having the top of the reactor open to provide free-surface flow of fluid in a "top open" channel.

The fluid treatment system taught in the Maarschalkerweerd #1 patents is characterized by having a free-surface flow of fluid (typically the top fluid surface was not purposely controlled or constrained). Thus, the systems would typically follow the behaviour of open channel hydraulics. Since the design of the system inherently comprised a free-surface flow of fluid, there were constraints on the maximum flow each lamp or lamp array could handle before either one or other hydraulically adjoined arrays would be adversely affected by changes in water elevation. At higher flows or significant changes in the flow, the unrestrained or free-surface flow of fluid would be allowed to change the treatment volume and cross-sectional shape of the fluid flow, thereby rendering the reactor relatively ineffective. Provided that the power to each lamp in the array was relatively low, the subsequent fluid flow per lamp would be relatively low. The concept of a fully open channel fluid treatment system would suffice in these lower lamp power and subsequently lower hydraulically loaded treatment systems. The problem here was that, with less powerful lamps, a relatively large number of lamps was required to treat the same volume of fluid flow. Thus, the inherent cost of the system would be unduly large and/or not competitive with the additional features of automatic lamp sleeve cleaning and large fluid volume treatment systems.

This led to the so-called "semi-enclosed" fluid treatment systems.

U.S. Pat. Nos. 5,418,370, 5,539,210 and Re36,896 (all in the name of Maarschalkerweerd and all assigned to the assignee of the present invention and hereinafter referred to as the Maarschalkerweerd #2 patents) all describe an improved radiation source module for use in gravity fed fluid treatment systems which employ UV radiation. Generally, the improved radiation source module comprises a radiation source assembly (typically comprising a radiation source and a protective (e.g., quartz) sleeve) sealingly cantilevered from a support member. The support member may further comprise appropriate means to secure the radiation source module in the gravity fed fluid treatment system.

Thus, in order to address the problem of having a large number of lamps and the incremental high cost of cleaning associated with each lamp, higher output lamps were applied for UV fluid treatment. The result was that the number of lamps and subsequent length of each lamp was dramatically reduced. This led to commercial affordability of automatic lamp sleeve cleaning equipment, reduced space requirements for the treatment system and other benefits. In order to use the more powerful lamps (e.g. medium pressure UV lamps), the hydraulic loading per lamp during use of the system would be increased to an extent that the treatment volume/cross-sectional area of the fluid in the reactor would significantly change if the reactor surface was not confined on all surfaces, and hence such a system would be rendered relatively ineffective. Thus, the Maarschalkerweerd #2 patents are characterized by having a closed surface confining the fluid being treated in the treatment area of the reactor. This closed treatment system had open ends which, in effect, were disposed in an open channel. The submerged or wetted equipment (UV lamps, cleaners and the like) could be extracted using pivoted hinges, sliders and various other devices allowing removal of equipment from the semi-enclosed reactor to the free surfaces.

The fluid treatment system described in the Maarschalkerweerd #2 patents was typically characterized by relatively short length lamps which were cantilevered to a substantially vertical support arm (i.e., the lamps were supported at one end only). This allowed for pivoting or other extraction of the lamp from the semi-enclosed reactor. These significantly shorter and more powerful lamps inherently are characterized by being less efficient in converting electrical energy to UV energy. The cost associated with the equipment necessary to physically access and support these lamps was significant.

Historically, the fluid treatment modules and systems described in the Maarschalkerweerd #1 and #2 patents have found widespread application in the field of municipal waste water treatment (i.e., treatment of water that is discharged to a river, pond, lake or other such receiving stream).

In the field of municipal drinking water, it is known to utilize so-called "closed" fluid treatment systems or "pressurized" fluid treatment systems.

Closed fluid treatment devices are known—see, for example, U.S. Pat. No. 5,504,335 (Maarschalkerweerd #3). Maarschalkerweerd #3 teaches a closed fluid treatment device comprising a housing for receiving a flow of fluid. The housing comprises a fluid inlet, a fluid outlet, a fluid treatment zone disposed between the fluid inlet and the fluid outlet, and at least one radiation source module disposed in the fluid treatment zone. The fluid inlet, the fluid outlet and the fluid treatment zone are in a collinear relationship with respect to one another. The at least one radiation source module comprises a radiation source sealably connected to a leg which is sealably mounted to the housing. The radiation source is disposed substantially parallel to the flow of fluid. The radiation source module is removable through an aperture provided in the housing intermediate to fluid inlet and the fluid outlet thereby obviating the need to physically remove the device for service of the radiation source.

U.S. Pat. No. 6,500,346 [Taghipour et al. (Taghipour)] also teaches a closed fluid treatment device, particularly useful for ultraviolet radiation treatment of fluids such as water. The device comprises a housing for receiving a flow of fluid. The housing has a fluid inlet, a fluid outlet, a fluid treatment zone disposed between the fluid inlet and the fluid outlet and at least one radiation source having a longitudinal axis disposed in the fluid treatment zone substantially transverse to a direction of the flow of fluid through the housing. The fluid inlet, the fluid outlet and the fluid treatment zone are arranged substantially collinearly with respect to one another. The fluid inlet has a first opening having: (i) a cross-sectional area less than a cross-sectional area of the fluid treatment zone, and (ii) a largest diameter substantially parallel to the longitudinal axis of the at least one radiation source assembly.

Practical implementation of known fluid treatment systems of the type described above has been such that the longitudinal axis of the radiation source is: (i) parallel to the direction of fluid flow through the fluid treatment system, or (ii) orthogonal to the direction of fluid flow through the fluid treatment system. Further, in arrangement (ii), it has been common to place the lamps in an array such that, from an upstream end to a downstream end of the fluid treatment system, a downstream radiation source is placed directly behind an upstream radiation source.

The use of arrangement (ii) in a UV radiation water treatment system has been based on the theory that radiation was effective up to a prescribed distance from the radiation source, depending on the transmittance of the water being treated. Thus, it has become commonplace to interspace the radiation sources in arrangement (ii) such that the longitudinal axes of adjacent radiation sources are spaced at a distance equal to approximately twice the prescribed distance mentioned in the previous sentence.

U.S. Pat. No. 5,503,800 [Free] teaches an ultraviolet sterilizing system for waste water adopting arrangement (ii) described above. In the system taught by Free, channels are formed around a single lamp assembly and projections are formed in the channels to induce turbulent plug flow such that when the apparatus is inserted into a flow of liquid to be treated, the channels act to confine and direct liquid about the housing and the projections act to establish a continuous, cyclical flow in the channels between housing and the channels walls. This system has disadvantages since it requires individual channels be provided between a wall structure and a single lamp assembly. Thus, when treating large volumes of water, it is necessary to utilize a plurality of radiation source assemblies. The arrangement taught by Free is quite complicated since each radiation source assembly would have to be configured to have a pair of opposed chambers as shown in Free and each chamber would have to have the projections required to establish the so-called plug flow of the liquid. This is not surprising since the aim of the Free system is to create a continuous, cyclical flow in the channels between housing and the channels walls.

U.S. Pat. No. 5,952,663 [Blatchley, III et al. (Blatchley)] teaches an apparatus for applying ultraviolet radiation dosage to fluids in an open channel. With particular reference to FIG. 12 in Blatchley, there is shown a fluid treatment channel containing a module having a series of vertically disposed lamps (14). Disposed on the sidewalls of the fluid channel are a series of fluid diverters (27). As shown, the arrangement of fluid diverters (27) is such that each fluid diverter (27) projects into the fluid treatment channel to the same extent. Such an arrangement is disadvantages since it results in relatively high fluid head loss and low treatment efficiency.

The deficiences in Free and Blatchely have been addressed in International Publication Number 2008/055344 [Ma et al. (Ma)] by providing an improved fluid treatment system. The improvement results from using an approach that is somewhat counterintuitive to the prior art approach. Specifically, the prior art approach of Blatchely was premised on using a flow diverter structure on the wall of the fluid treatment zone to direct fluid (typically water) being treated from the wall toward the center of the fluid treatment zone in which there is disposed a series of radiation source assemblies. Contrary to this approach, the present fluid treatment systems uses a combination of the radiation source assembly and a prescribed wall structure to encourage fluid flow along the sides of the walls of the fluid treatment zone while obviating or mitigating short circuiting (i.e., the phenomon where fluid travel along the wall is not subject to a sufficient dose of radiation). Thus, unlike the prior art approach which seeks to concentrate fluid flow toward the middle of the fluid treatment zone, fluid treatment system taught by Ma relies on relatively uniform fluid flow from side to side in the fluid treatment zone while obviating or mitigating short circuiting.

While the fluid treatment system taught by Ma represents a significant improvement in the art, there is room for improvement. Specifically, practical implementations of fluid treatment systems such as those in accordance with arrangement (ii) described above (particularly those taught by Blatchley and Ma having diverting or other structures projecting from the side walls of the open channel into the fluid treatment zone) involve the use of relatively long radiation sources that need to be placed very close to the side walls of the of the open channel. This leads to the significant likelihood that the radiation sources will be damage through inadvertent contact with the side—e.g., as the radiation sources are installed or extracted from the fluid treatment system. It is also advantageous to maintain a tight tolerance for the prescribed distance between the radiation source and the side wall to ensure optimal performance of the reactor. Such a tolerance can be achieved when the reactor module is manufactured as a single unit. A final consideration is that since treatment channels are becoming narrower and pre-manufactured sealable housing will be easier to install.

It would be highly desirable to have a radiation source module and a fluid treatment system that overcomes the above problems.

SUMMARY OF THE INVENTION

It is an object of the present invention to obviate or mitigate at least one of the above-mentioned disadvantages of the prior art.

It is another object of the present invention to provide a novel radiation source module.

It is another object of the present invention to provide a novel fluid treatment system.

Accordingly, in one of its aspects, the present invention provides a radiation source module for use in a fluid treatment system, the radiation source module comprising:

a housing having an inlet, an outlet and a fluid treatment zone disposed between; the fluid treatment zone comprising a first wall surface and a second wall surface interconnected by a floor surface, the first wall surface, the second wall surface and the floor surface configured to received a flow of fluid through the fluid treatment zone;

at least one radiation source assembly secured with respect to the first wall surface and the second wall surface; and a module motive coupling element connected to the housing and configured to be coupled to a module motive element to permit the radiation source module to be installed in and extracted from the fluid treatment system In another of its aspects, the present invention provides a fluid treatment system comprising:

an open channel for receiving a flow of fluid;
at least one radiation source module comprising:
a housing having an inlet, an outlet and a fluid treatment zone disposed between; the fluid treatment zone comprising a first wall surface and a second wall surface interconnected by a floor surface, the first wall surface, the second wall surface and the floor surface configured to received a flow of fluid through the fluid treatment zone;
at least one radiation source assembly secured with respect to the first wall surface and the second wall surface; and
a module motive element connected to the housing and configured to permit to be installed in and extracted from the fluid treatment system.

Thus, the present inventors have discovered a novel radiation source module which obviates or mitigates the above-disadvantages of the prior art.

Specifically, the present radiation source module is, on the one hand, moveable in and out of the open channel in which fluid is flowing, while on the other hand, able to act as an independent fluid treatment system in that it contains sidewalls and a floor element which cooperate to contain a flow of fluid in which radiation source assemblies are disposed. While many of the embodiments disclosed below utilize distinct sidewalls and floor portions in the radiation source module to achieve this goal, it will be appreciated by those of skill in the art that the use of sidewalls and floor elements is not particularly required and, for example, a cross-sectional shape of the treatment area of the radiation source module could be somewhat continuous or curvilinear so as not to contain distinct sidewalls and floor elements yet still function in accordance with the teachings of the present invention. Such modifications are of course encompassed by the present invention.

Further, the illustrated embodiments below result in fluid passing through the radiation source module and being unconstrained on an upper surface of the fluid flowing through the radiation source module. These embodiments may be modified to provide a fluid radiation source module in which all surfaces of the fluid travelling there through are confined thereby presenting a substantially closed cross-section to the flow of fluid. Again, these modifications are encompassed by the present invention.

Finally, in the illustrated embodiments, module removal devices are illustrated which remove the radiation source module from the fluid treatment system by rotation or linear translation. Of course, it may be possible to modify these specific embodiments to achieve removal of the radiation source module without relying only on rotation or linear translation. Again, these modifications are encompassed by the present invention.

BRIEF DESCRIPTION OF THE DRAWINGS

Embodiments of the present invention will be described with reference to the accompanying drawings, wherein like reference numerals denote like parts, and in which.

DETAILED DESCRIPTION OF THE PREFERRED EMBODIMENTS

Figure 1:
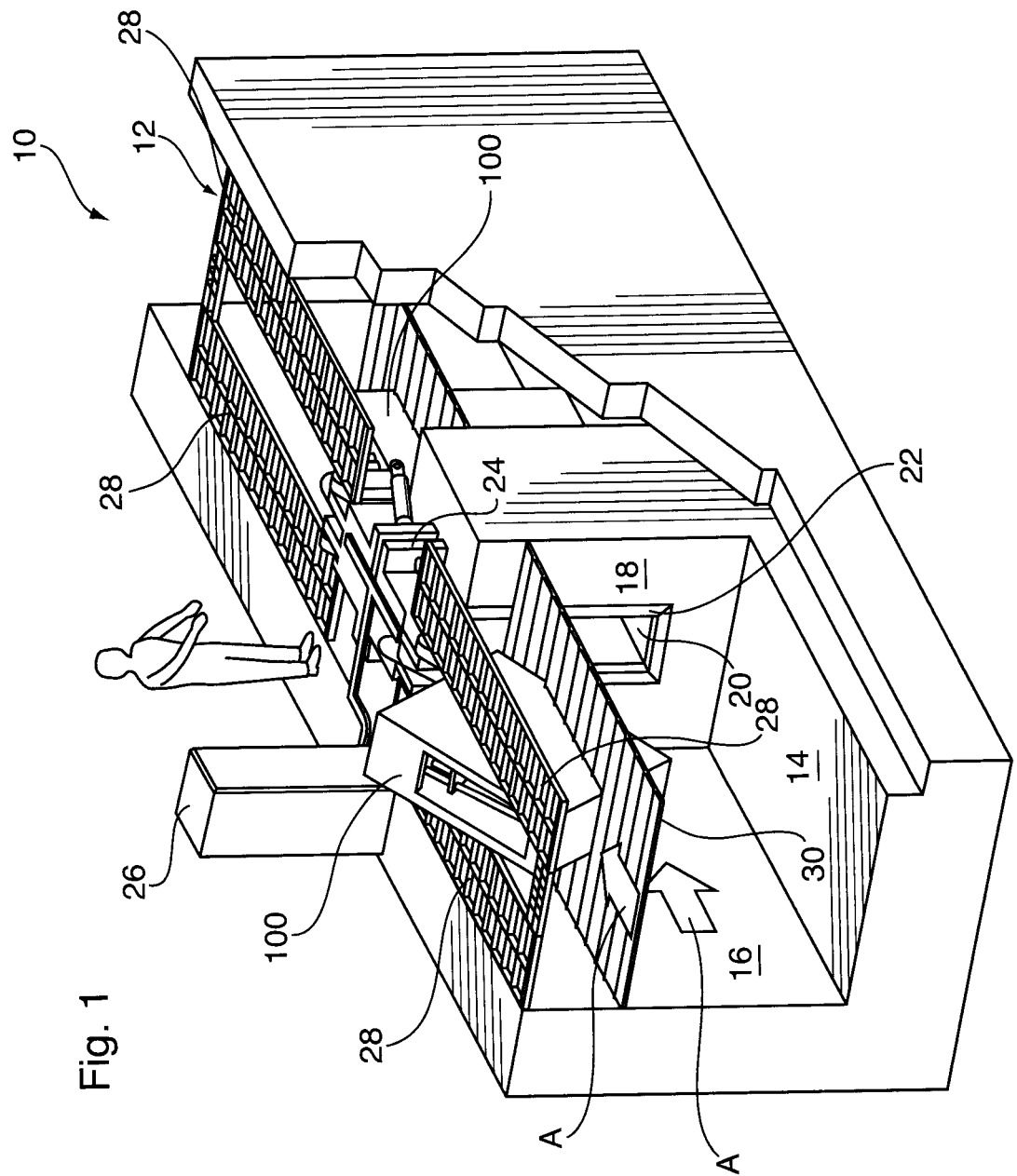
FIGS. 1-21 illustrate various preferred embodiments of the present fluid treatment system and the present radiation source module.

In one of its aspects, the present invention relates to a radiation source module for use in a fluid treatment system, the radiation source module comprising:

a housing having an inlet, an outlet and a fluid treatment zone disposed between; the fluid treatment zone comprising a first wall surface and a second wall surface interconnected by a floor surface, the first wall surface, the second wall surface and the floor surface configured to received a flow of fluid through the fluid treatment zone;

at least one radiation source assembly secured with respect to the first wall surface and the second wall surface; and a module motive coupling element connected to the housing and configured to be coupled to a module motive element to permit the radiation source module to be installed in and extracted from the fluid treatment system.

Preferred embodiments of this radiation source module may include any one or a combination of any two or more of any of the following features:

the first wall surface is removable with respect to the housing;
the second side wall surface is removable with respect to the housing;
the housing further comprises a top surface interconnecting the first wall surface and the second wall surface;
the top portion, floor portion, first wall surface and the second wall surface combining to define an enclosure having substantially closed cross-section to receive the flow of fluid;

the first wall surface comprises a first fluid deflector element projecting into the fluid treatment zone;

the first wall surface comprises a plurality of first fluid deflector elements projecting into the fluid treatment zone;

the plurality of first fluid deflector elements are in a spaced relationship along the first wall surface with respect to the direction of fluid flow through the fluid treatment zone;

second wall surface comprises a second fluid deflector element projecting into the fluid treatment zone;

second wall surface comprises a plurality of second fluid deflector elements projecting into the fluid treatment zone;

the plurality of second fluid deflector elements are in a spaced relationship along the second wall surface with respect to the direction of fluid flow through the fluid treatment zone the first wall surface comprises a first receptacle portion;

the first wall surface comprises a plurality of first receptacle portions;

the plurality of first receptacle portions are in a spaced relationship along the first wall surface with respect to the direction of fluid flow through the fluid treatment zone;

second wall surface comprises a second receptacle portion;

second wall surface comprises a plurality of second receptacle portions;

the plurality of second receptacle portions are in a spaced relationship along the second wall surface with respect to the direction of fluid flow through the fluid treatment zone;

the housing comprises a seal element configured to contact a surface of the fluid treatment system;

the radiation source module comprises a plurality of radiation source assemblies secured with respect to the pair of opposed side walls;

each radiation source assembly comprises a radiation source;

the radiation source is disposed in a protective sleeve;

the protective sleeve comprises a closed end and an open end;

each radiation source assembly comprises an ultraviolet radiation source;

each radiation source assembly comprises a low pressure high output ultraviolet radiation source;

the first wall surface and the second wall surface are substantially parallel to one another; and the radiation source assembly may be cantilevered (i.e., unsupported at a distal end) or supported at both ends.

In another of its aspects, the present invention relates to a fluid treatment system comprising:

an open channel for receiving a flow of fluid;

at least one radiation source module comprising:

a housing having an inlet, an outlet and a fluid treatment zone disposed between; the fluid treatment zone comprising a first wall surface and a second wall surface interconnected by a floor surface, the first wall surface, the second wall surface and the floor surface configured to received a flow of fluid through the fluid treatment zone;

at least one radiation source assembly secured with respect to the first wall surface and the second wall surface; and a module motive element connected to the housing and configured to permit to be installed in and extracted from the fluid treatment system.

Preferred embodiments of this fluid treatment system may include any one or a combination of any two or more of any of the following features:

the housing comprises a seal element configured to provide a substantially fluid tight seal between the housing and a surface of the open channel;

the housing comprises a seal element configured to provide a substantially fluid tight seal between the housing and a side wall surface of the open channel;

the housing comprises a seal element configured to provide a substantially fluid tight seal between the housing and a floor surface of the open channel;

the housing comprises a seal element configured to provide a substantially fluid tight seal between the housing and all surfaces of the open channel adjacent to the housing;

a bulkhead element is disposed in the open channel, the bulkhead element having a bulkhead inlet and a bulkhead outlet, the outlet of the housing configured to be disposed in fluid communication with the bulkhead inlet;

a bulkhead element is disposed in the open channel, the bulkhead element having a bulkhead inlet and a bulkhead outlet, the inlet of the housing configured to be disposed in fluid communication with the bulkhead outlet;

a bulkhead element is disposed in the open channel, the bulkhead element having an bulkhead inlet and a bulkhead outlet, and a pair of radiation source modules are configured to be disposed in the open channel such that: (i) the outlet of the housing of a first radiation source module is configured to be disposed in fluid communication with the bulkhead inlet, and (ii) the inlet of the housing of a second radiation source module is configured to be disposed in fluid communication with the bulkhead outlet.

the bulkhead element comprises a bulkhead seal configured to provide a substantially fluid tight seal between the bulkhead element and a surface of the radiation source module adjacent thereto;

the fluid treatment system further comprises a module motive element configured to be reversibly coupled to the module motive coupling element of the radiation source module;

the module motive element is configured to rotate the radiation source module with respect to the open channel;

the module motive element is configured to translate the radiation source module with respect to the open channel;

the first wall surface is removable with respect to the housing;

the second side wall surface is removable with respect to the housing;

the floor surface is removable with respect to the housing;

the housing further comprises a top surface interconnecting the first wall surface and the second wall surface; the top portion, floor portion, first wall surface and the second wall surface combining to define an enclosure having substantially closed cross-section to receive the flow of fluid;

the first wall surface comprises a first fluid deflector element projecting into the fluid treatment zone;

the first wall surface comprises a plurality of first fluid deflector elements projecting into the fluid treatment zone.

the plurality of first fluid deflector elements are in a spaced relationship along the first wall surface with respect to the direction of fluid flow through the fluid treatment zone;

second wall surface comprises a second fluid deflector element projecting into the fluid treatment zone;

second wall surface comprises a plurality of second fluid deflector elements projecting into the fluid treatment zone;

the plurality of second fluid deflector elements are in a spaced relationship along the second wall surface with respect to the direction of fluid flow through the fluid treatment zone;

wherein the first wall surface comprises a first receptacle portion;

the first wall surface comprises a plurality of first receptacle portions;

the plurality of first receptacle portions are in a spaced relationship along the first wall surface with respect to the direction of fluid flow through the fluid treatment zone;

The fluid treatment system as per the above, wherein the second wall surface comprises a second receptacle portion;

the second wall surface comprises a plurality of second receptacle portions;

the plurality of second receptacle portions are in a spaced relationship along the second wall surface with respect to the direction of fluid flow through the fluid treatment zone;

the housing comprises a seal element configured to contact a surface of the fluid treatment system;

the radiation source module in the fluid treatment system comprises a plurality of radiation source assemblies secured with respect to the pair of opposed side walls;

each radiation source assembly comprises a radiation source;

the radiation source is disposed in a protective sleeve;

the protective sleeve comprises a closed end and an open end;

each radiation source assembly comprises an ultraviolet radiation source;

each radiation source assembly comprises a low pressure high output ultraviolet radiation source; and the first wall surface and the second wall surface are substantially parallel to one another.

With reference to FIGS. 1-5, there is illustrated a fluid treatment system 10. Fluid treatment system 10 comprises an open channel 12. Open channel 12 comprises a channel floor 14 and a pair of a channel side walls 16.

Disposed in open channel 10 is a bulkhead 18 having an opening 20. Surrounding opening 20 is a seal element 22. A module removal device 24 is disposed on top of bulkhead 18. An electrical control panel 26 is disposed to one side of open channel 10. A series of grates 28 are disposed across open channel 10 near the top of channel side walls 16.

A pair of radiation source modules 100 are disposed in open channel 10 on either side of bulkhead 18. The nature of radiation source modules 100 will be described in more detail below. As illustrated, upstream radiation source module 100 is partially withdrawn from its so-called "in use" position in open channel 10 whereas downstream radiation source module 100 is in a so-called "in use" position with respect to bulkhead 18 and open channel 12.

In use, a flow of fluid, typically gravity fed, enters open channel 12 and flows in the direction of arrows A resulting in a fluid level 30.

Figure 2:
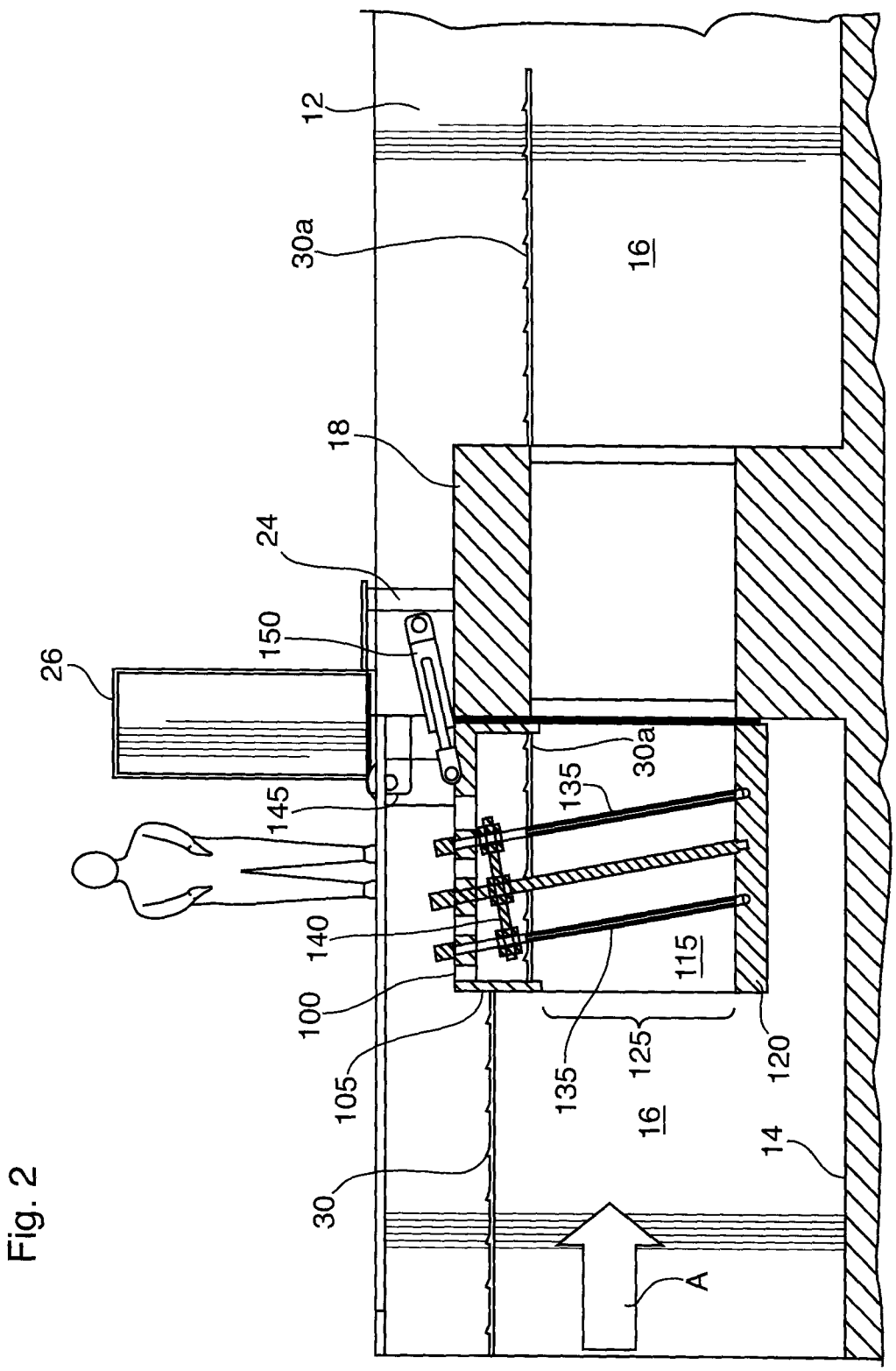

With particular reference to FIG. 2, it will be seen that upstream radiation source module 100 is shown in a so-called "in use" position whereas downstream radiation source module 100 shown in FIG. 1 has not been shown for clarity purposes only.

As illustrated, radiation source module 100 comprises a housing 105. Housing 105 comprises a pair of module sidewalls 110,115 and a module floor 120 interconnecting module sidewalls 110,115. Housing 105 further comprises a fluid inlet 125 and a fluid outlet 130.

It will be appreciated that the combination of module sidewalls 110,115 and module floor 120 combine to confine fluid entering housing 105 to define a fluid treatment zone. Disposed in this fluid treatment zone are a series of radiation source assemblies 135. It can be seen that radiation source assemblies 135 have a longitudinal access which is disposed substantially transverse to the direction of fluid flow through open channel 12 of fluid treatment system 10.

A cleaning system 140 is coupled to radiation source assemblies 135 and is movable from a retracted position to an extended position to remove undesirable material from the exterior of radiation source assemblies 135.

Figure 7:
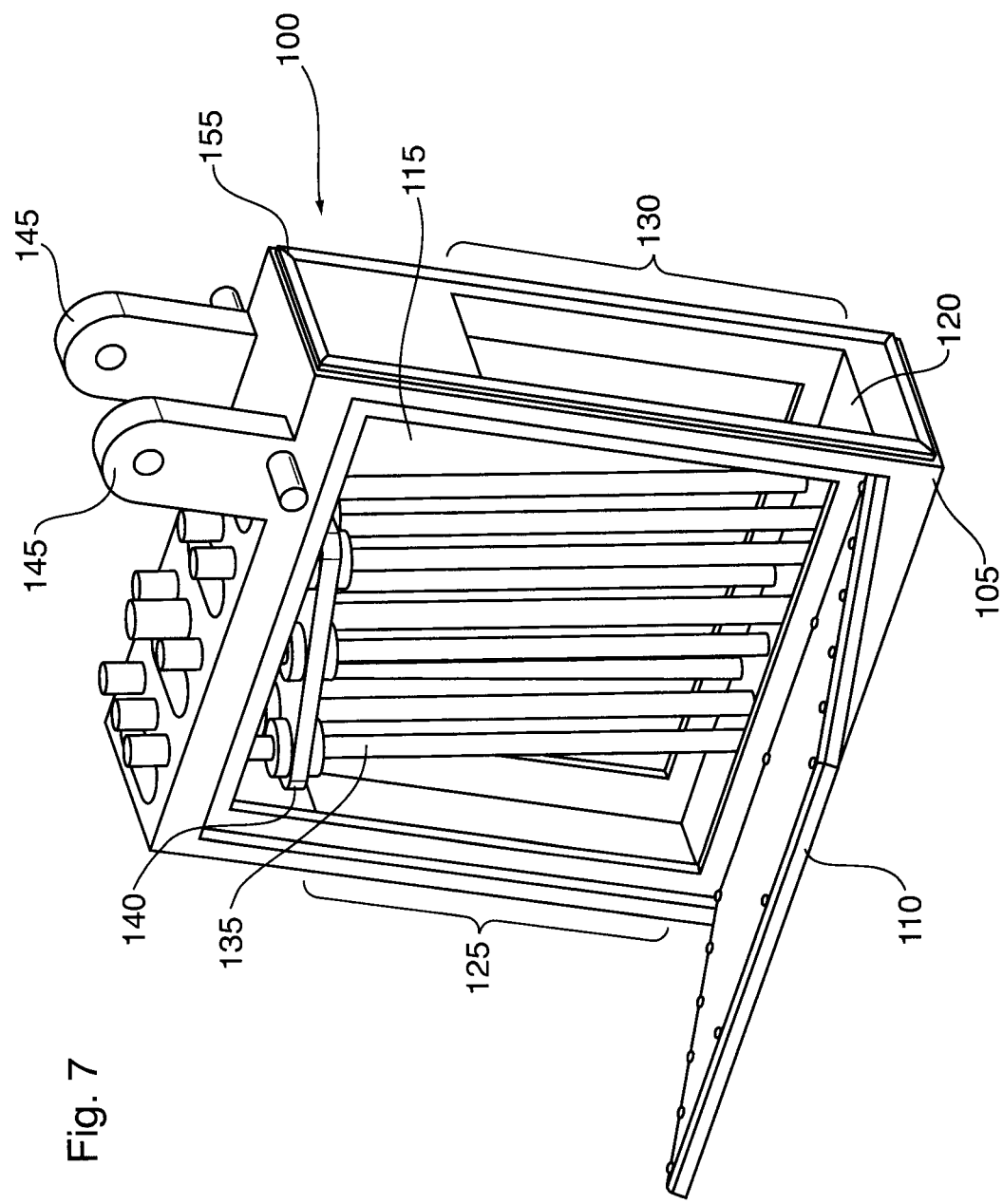
Figure 8:
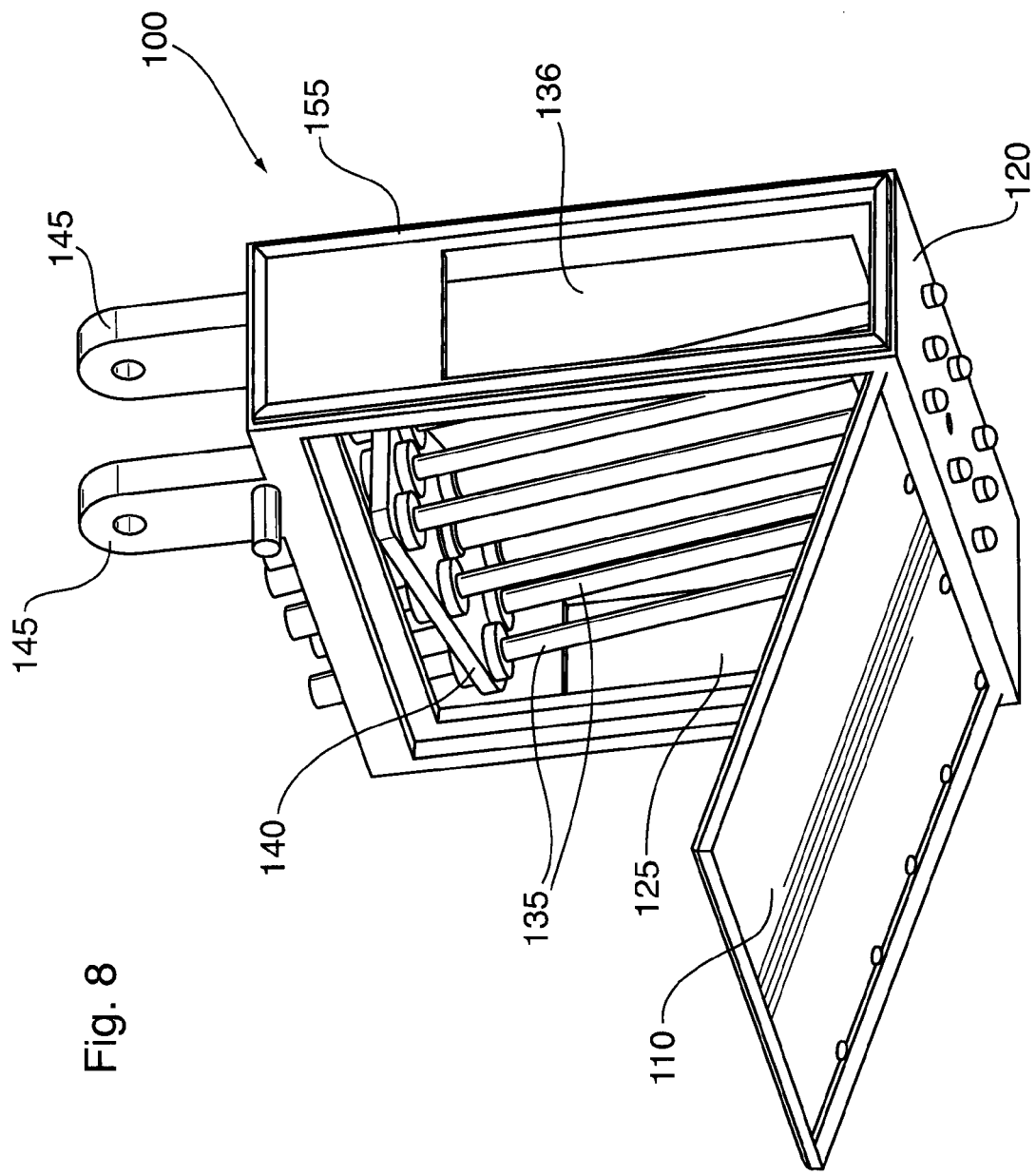
Figure 9:
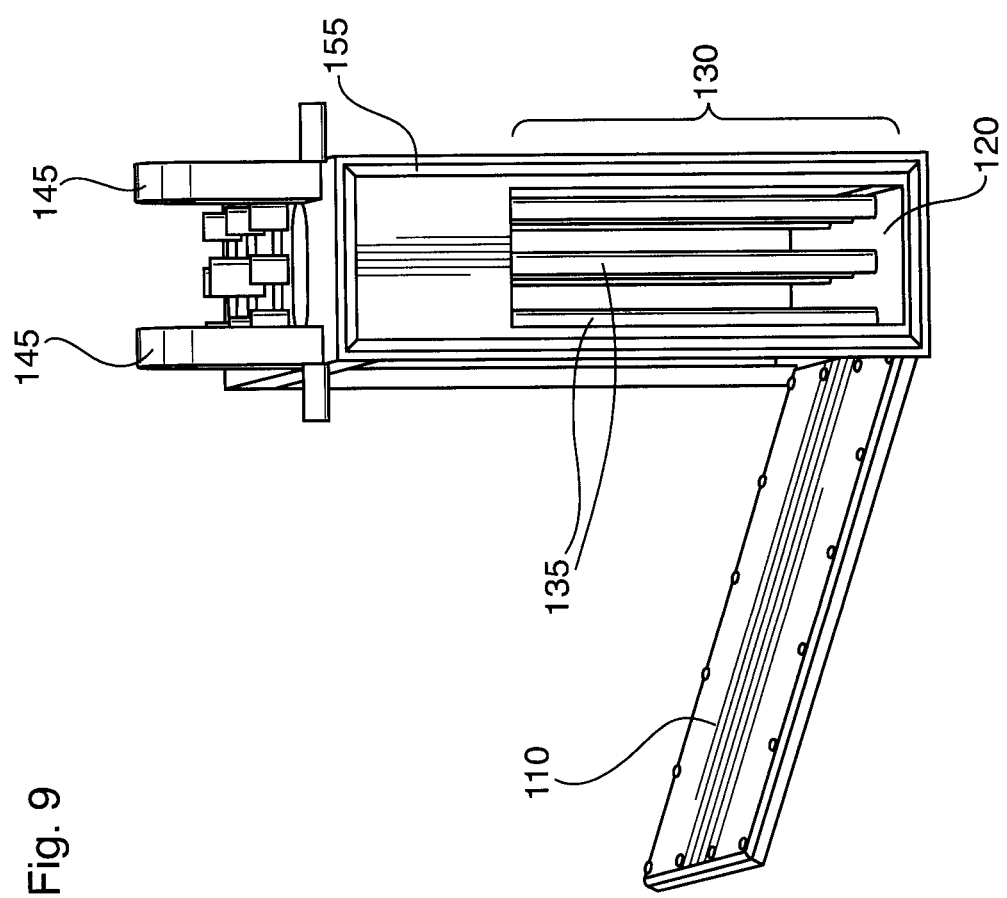

With particular reference to FIGS. 7 to 9, it can be seen that module sidewall 110 of housing 105 is removable to allow access to radiation source assemblies 135 and cleaning system 140. Module sidewall 115 and floor surface 120, is similarly removable but these are not shown for clarity purposes.

Disposed at the top of housing 105 are a pair of pivot elements 145. Pivot elements 145 are connected to a hydraulic cylinder 150 which is connected to module removal device 24.

Disposed around the periphery of fluid outlet 130 is a seal element 155 shown in FIG. 7. Seal element 155 is positioned and dimensioned to cooperate with seal element 22 on bulkhead 18 to provide a substantial fluid tight seal between housing 105 and bulkhead 18.

Although the interior surfaces of sidewalls 110,115 are shown as being smooth, it is possible to modify the interior surface of these sidewalls to adopt one more fluid deflector elements and/or receptacles, for example, as described in Ma.

With continued reference to FIG. 2, it can been seen that, when fluid enters housing 105 of radiation source module 100, a lower fluid level 30a is assumed. It will also be seen that in the illustrated embodiment, in essence, housing 105 of radiation source module 100 acts as a small open channel fluid treatment system in that fluid level 30a is unconstrained by any physical structure of radiation source module 100.

Figure 3:
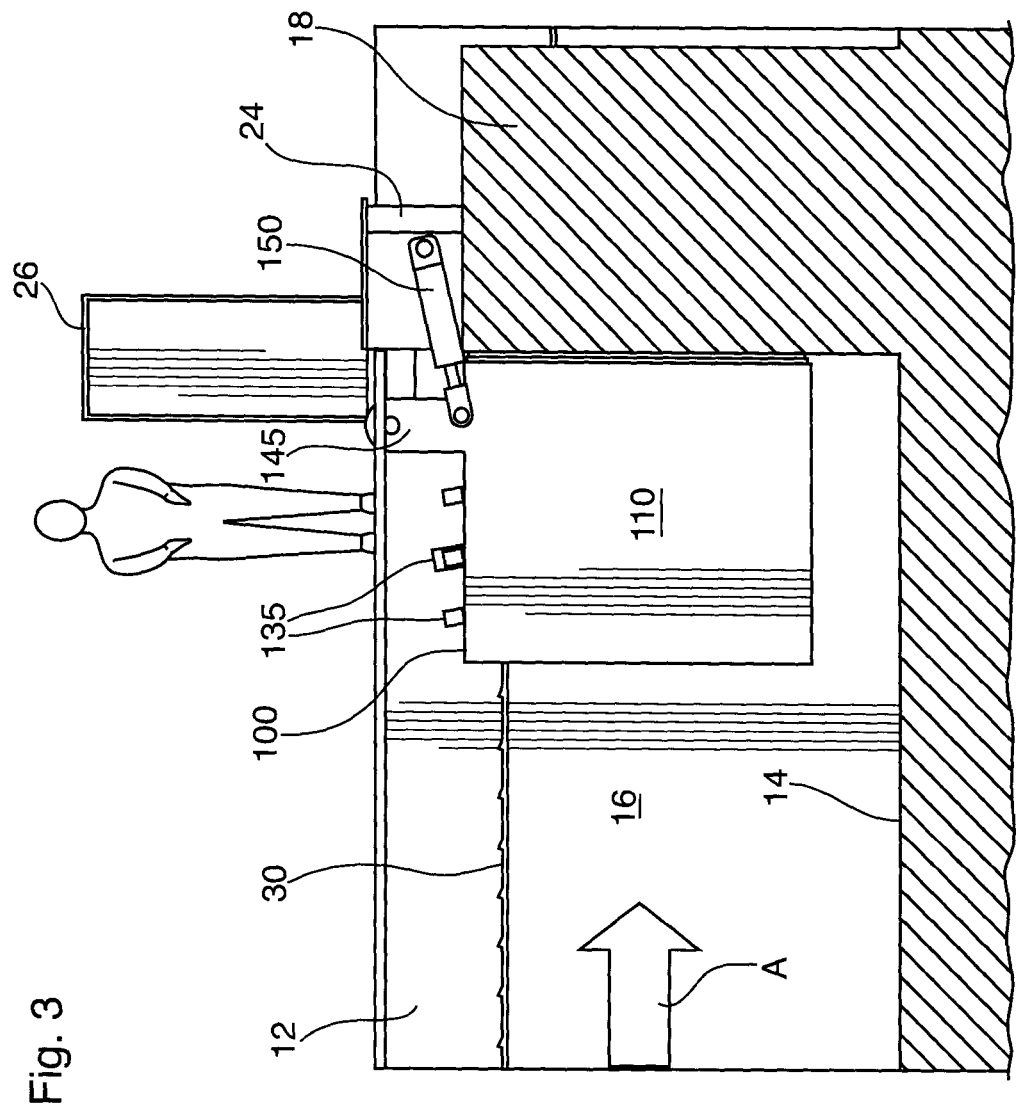
Figure 4:
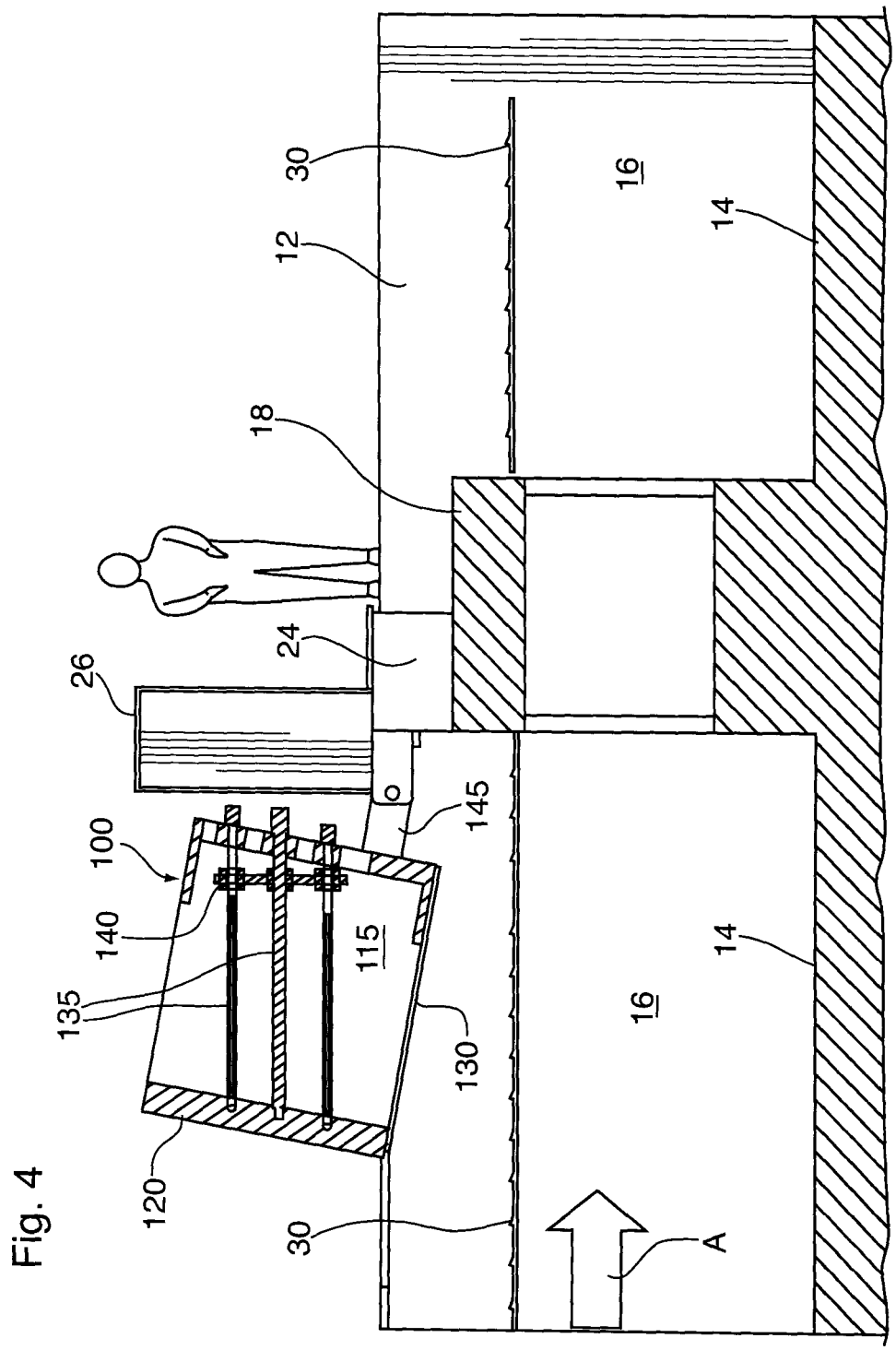
Figure 5:
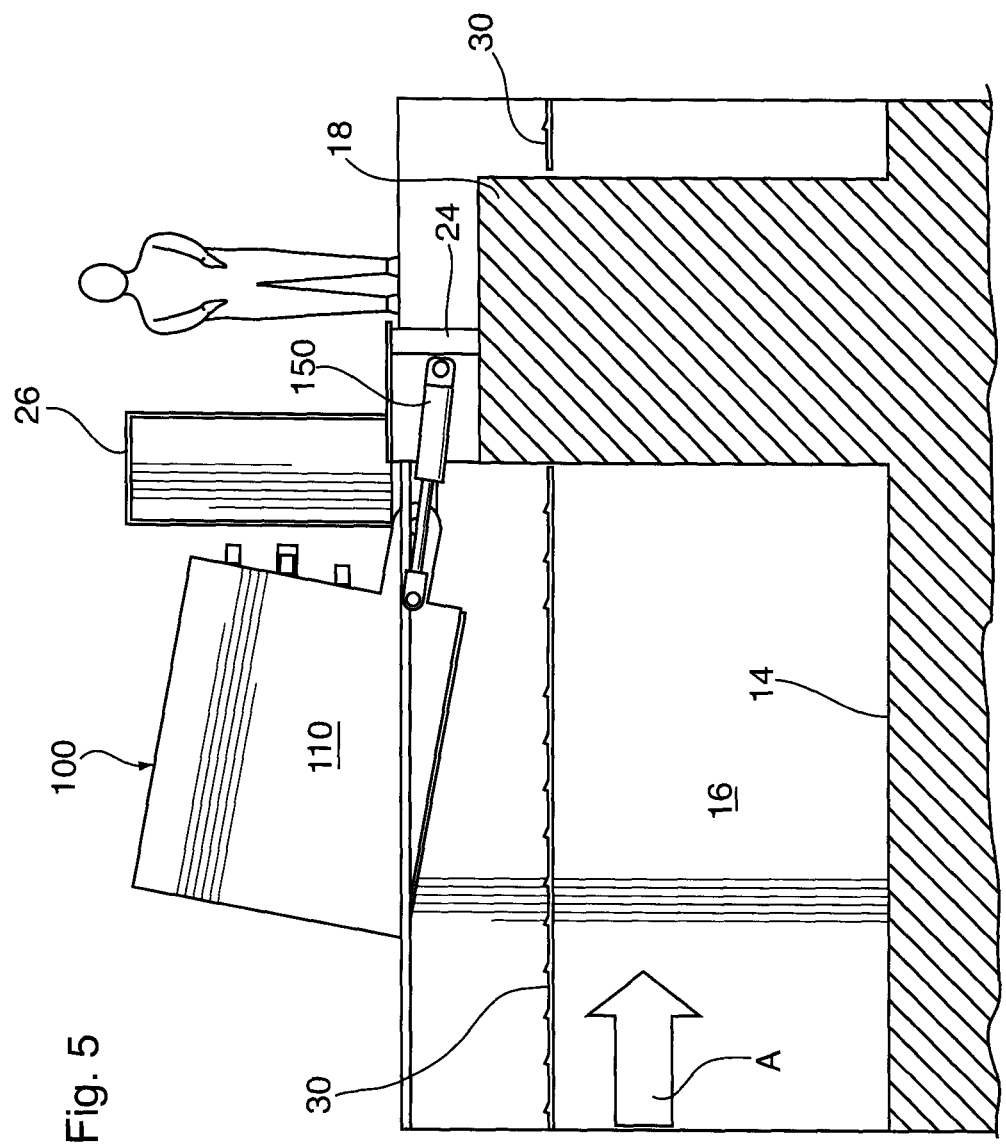

With reference to FIG. 4, when it is desired to extract radiation source module 100 from open channel 12, hydraulic cylinder 150 shown in FIGS. 2 and 3 (not shown in FIG. 4 for clarity) is extended which has the effect of pivoting radiation source module 100 out of open channel 12. In FIG. 4, again for clarity, downstream radiation source module 100 shown in FIG. 1 has not been illustrated. See also FIG. 5 which shows the same view as FIG. 4 except in FIG. 5, sidewall 110 of housing 105 of radiation source module 100 is shown in place.

Figure 6:
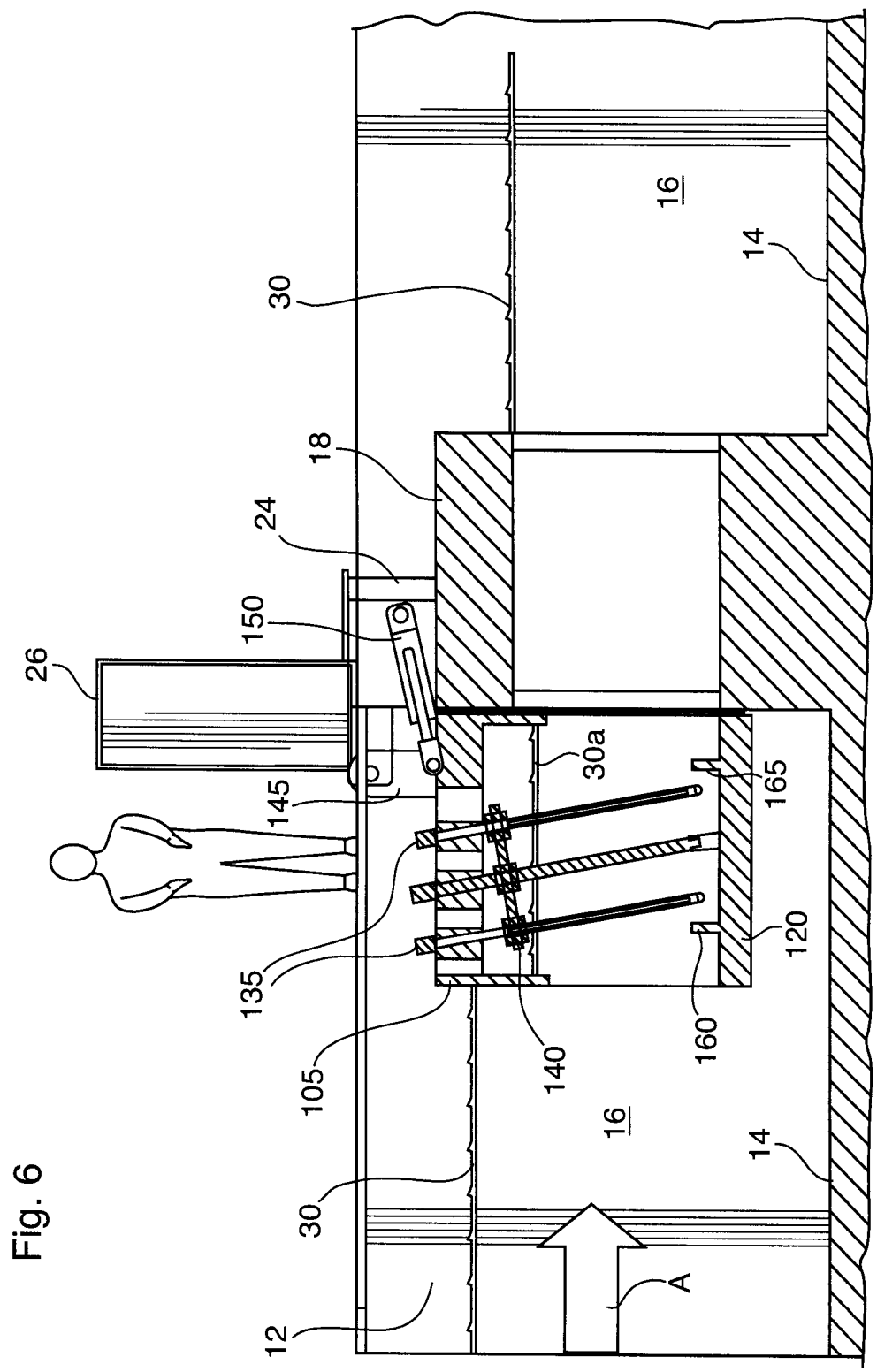

FIG. 6 illustrates a modification of the embodiment discussed above with reference to FIG. 5. Specifically, housing 105 of radiation source module 100 has been modified to include a pair of upstanding baffle plates 160 upstream and 165 downstream of the distal portions of radiation source assemblies 135. The use of such baffle plates is discussed in more detail in co-pending International Patent Publication Number WO 2010/102383 A1.

Figure 10:
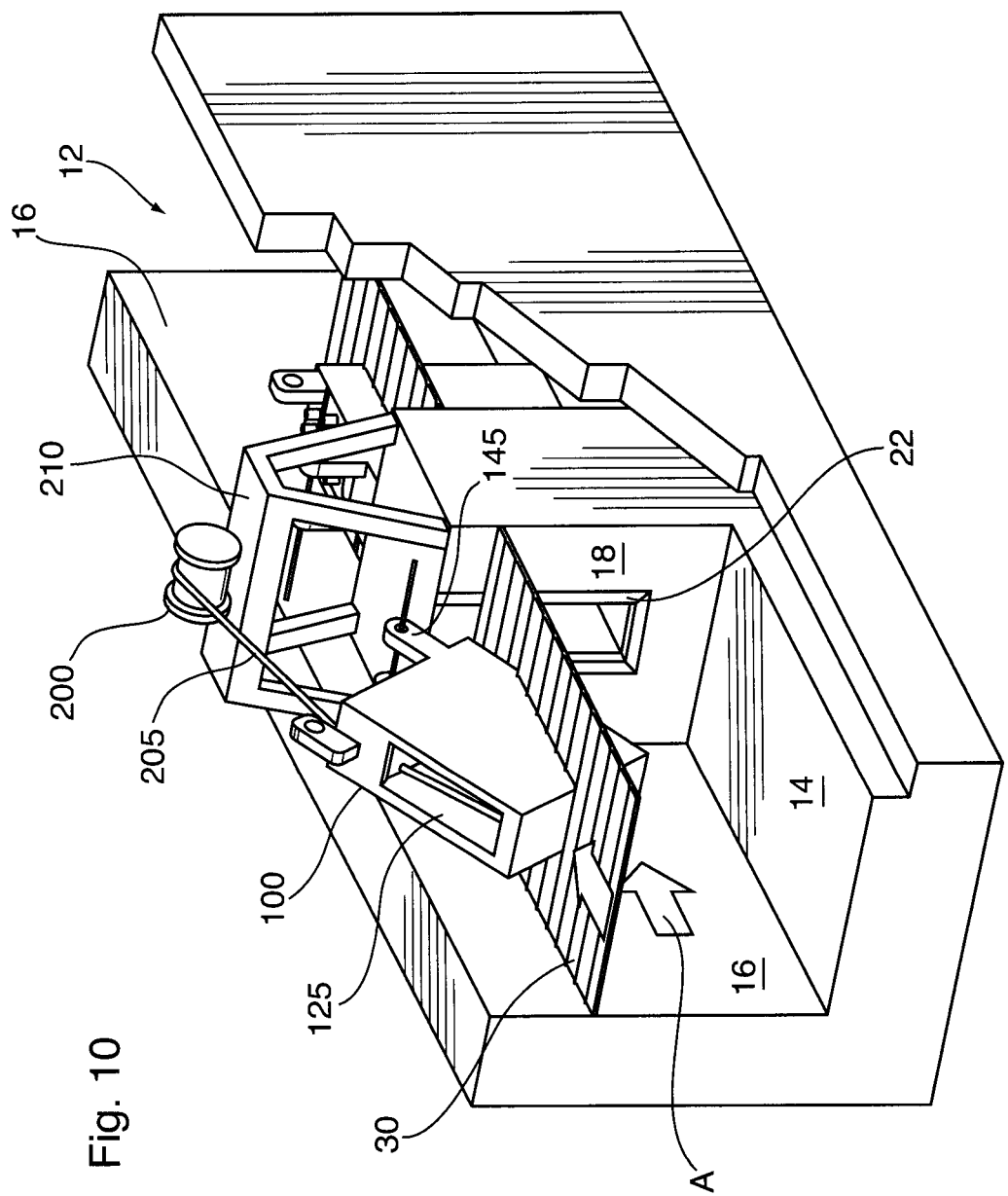
Figure 11:
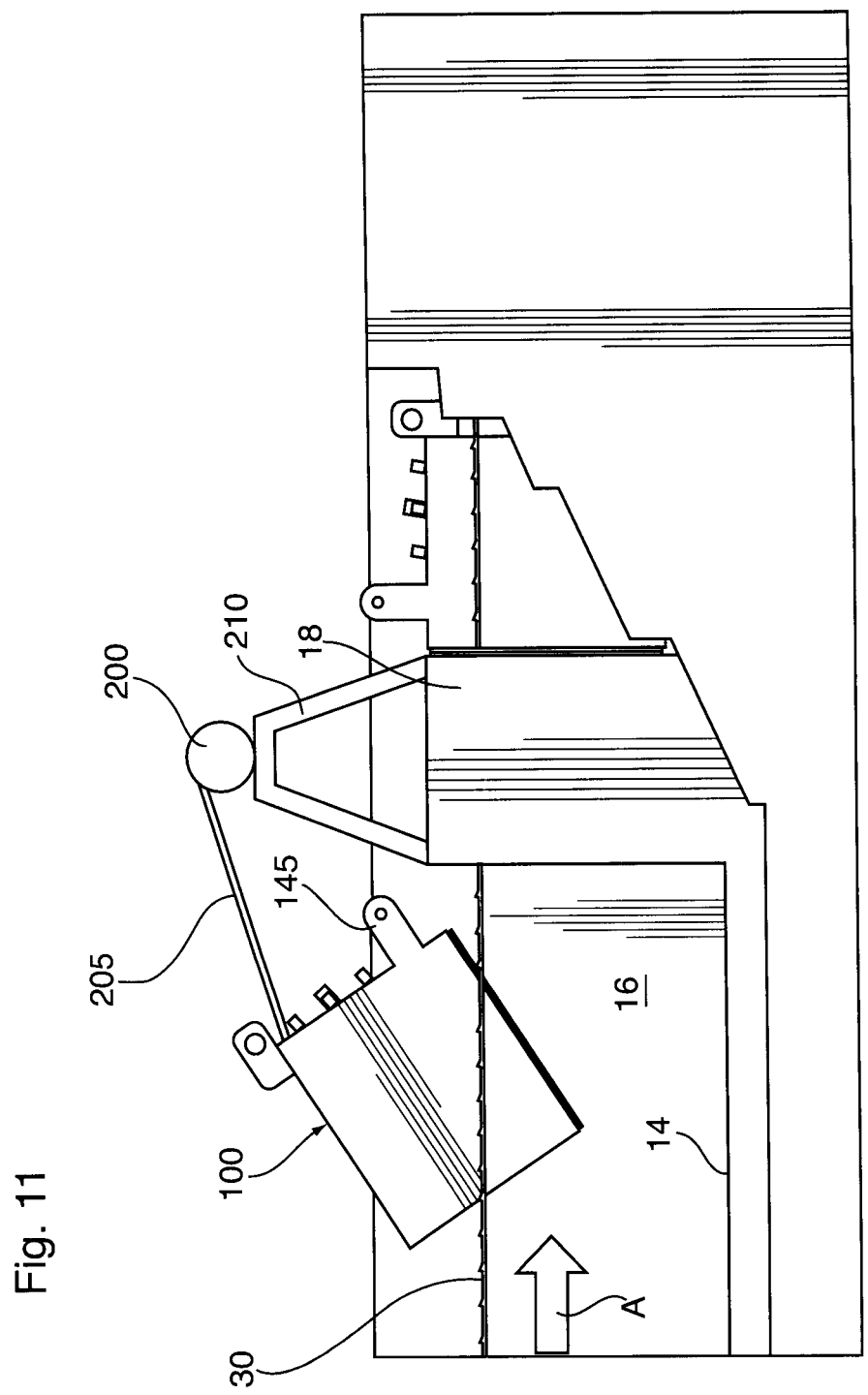

With reference to FIGS. 10-11, there is illustrated a modification to radiation source module 100 illustrated in FIGS. 1-9. Specifically, in FIG. 10, radiation source module 100 has been modified to rotate out of open channel 10 using a winch 200 (or similar element) and cable 205 disposed on a winch module 210. All other aspects of fluid radiation system 10 and radiation source module 100 are similar to those discussed above.

Figure 12:
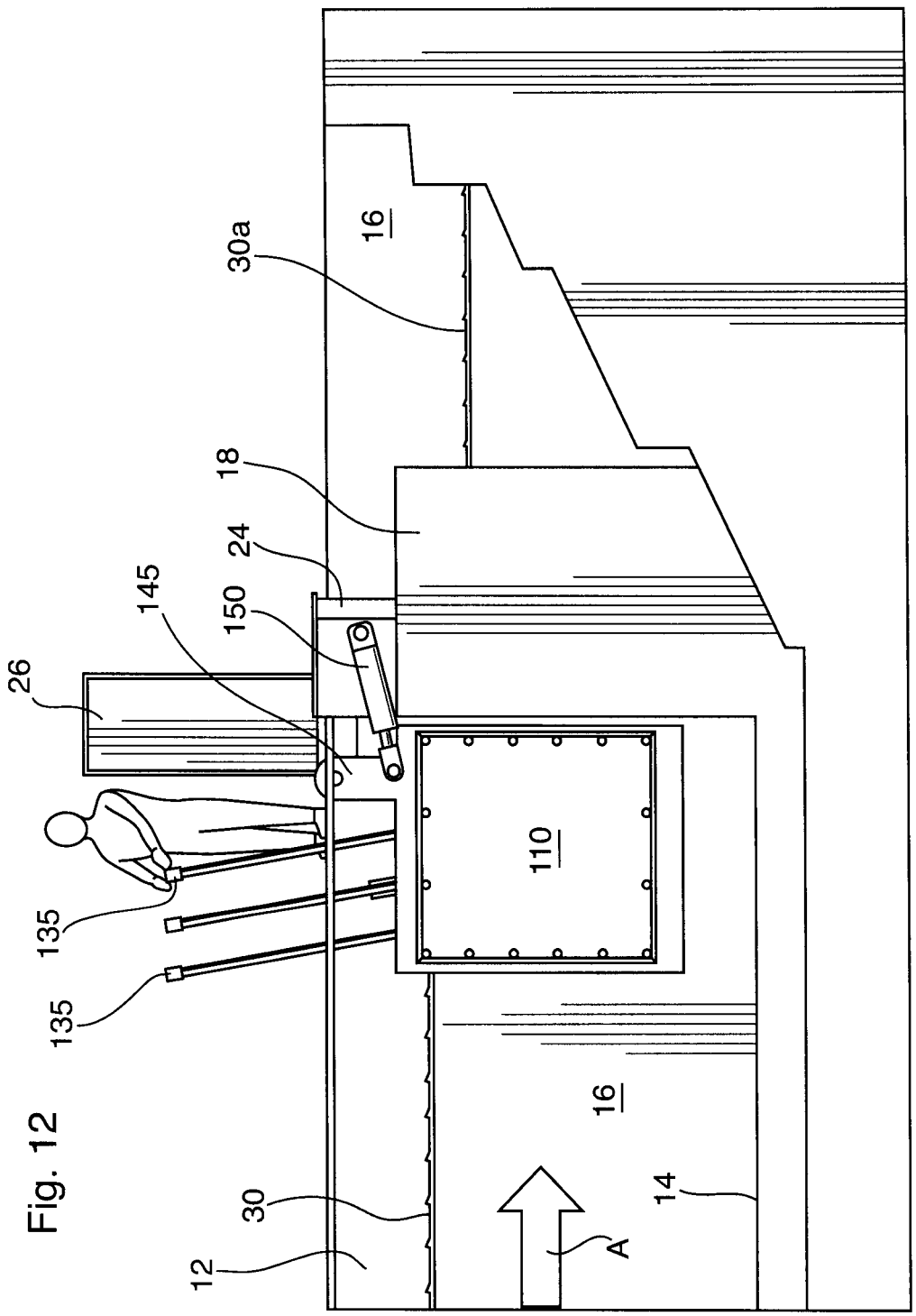

With reference to FIG. 12, there is shown an illustration of servicing of one or more radiation source assemblies 135 while radiation source module is maintained in position in open channel 12. In other words, it should be clear that extraction of entire radiation source module 100 from open channel 12 is not required to service radiation source assemblies 135.

Figure 13:
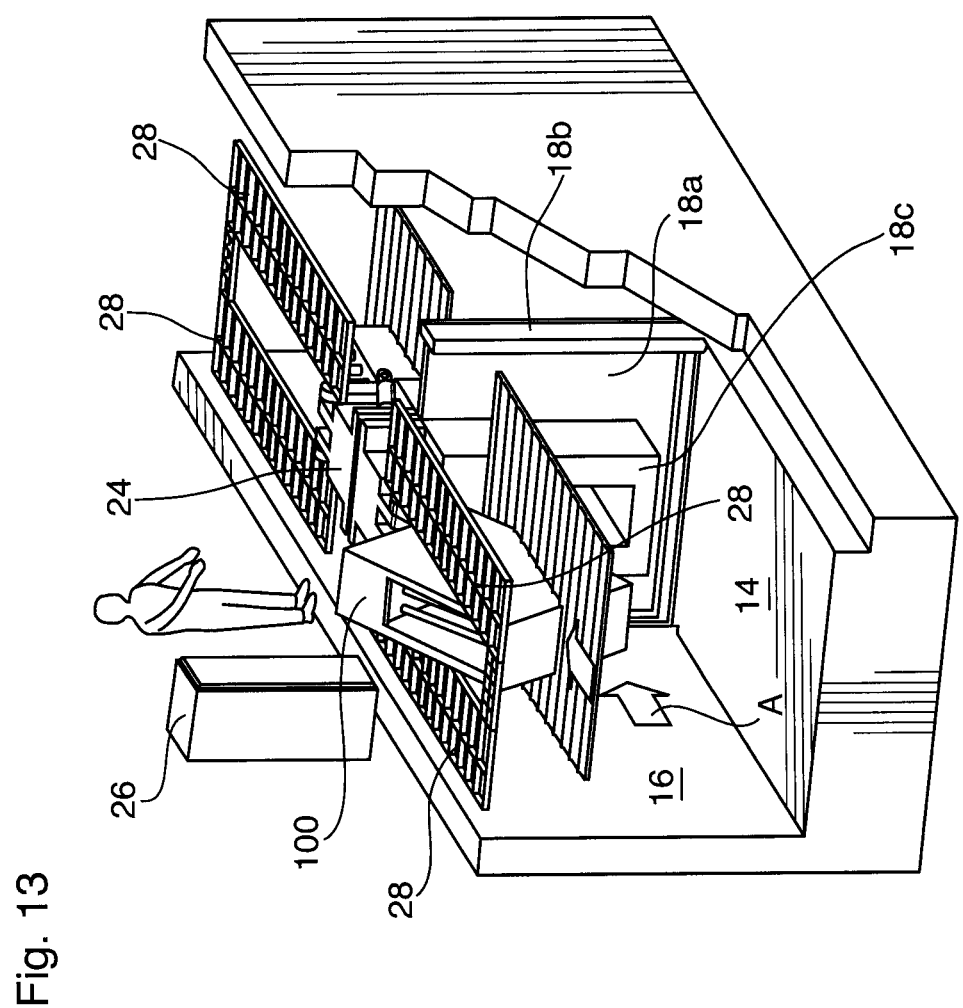
Figure 14:
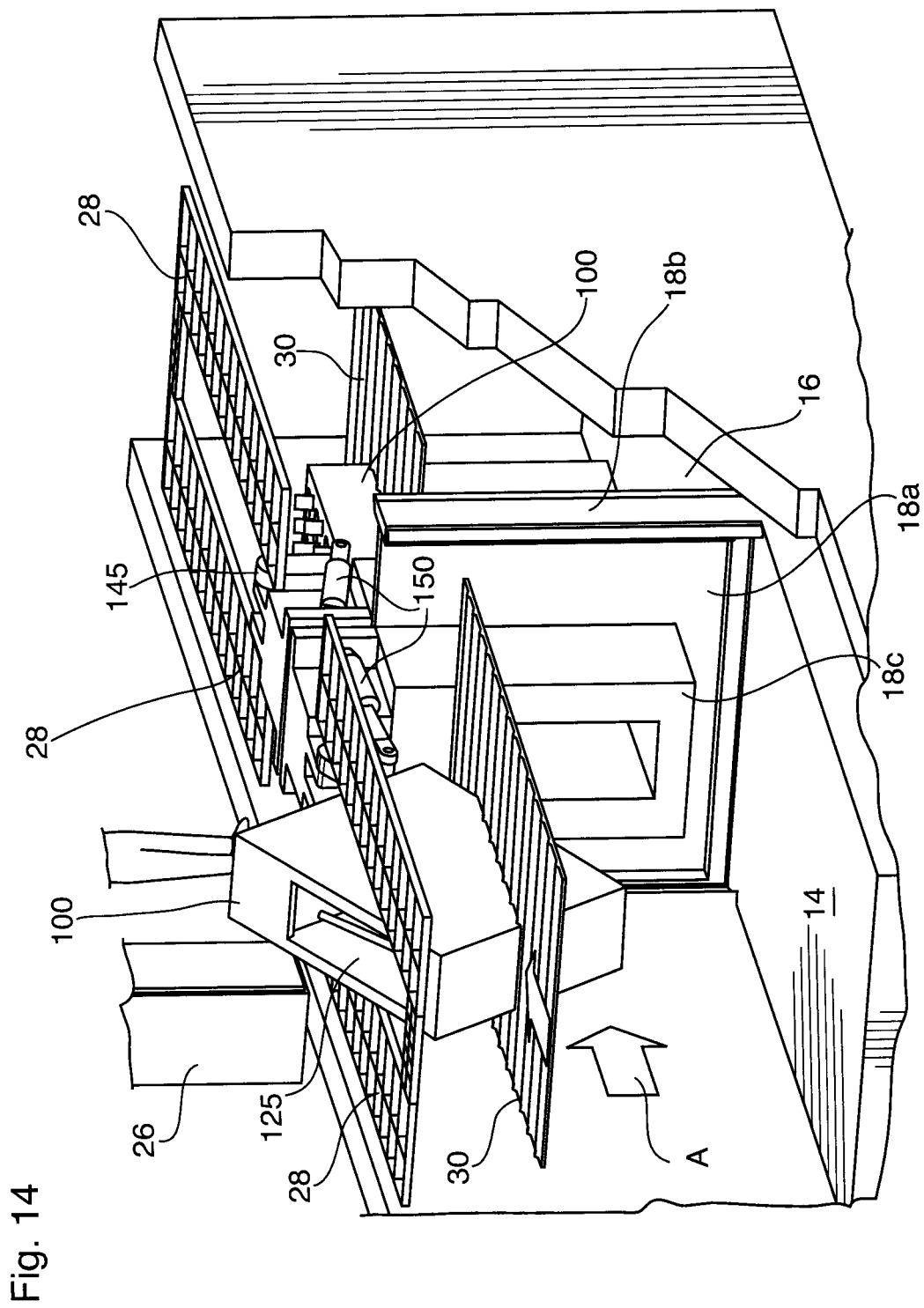
Figure 15:
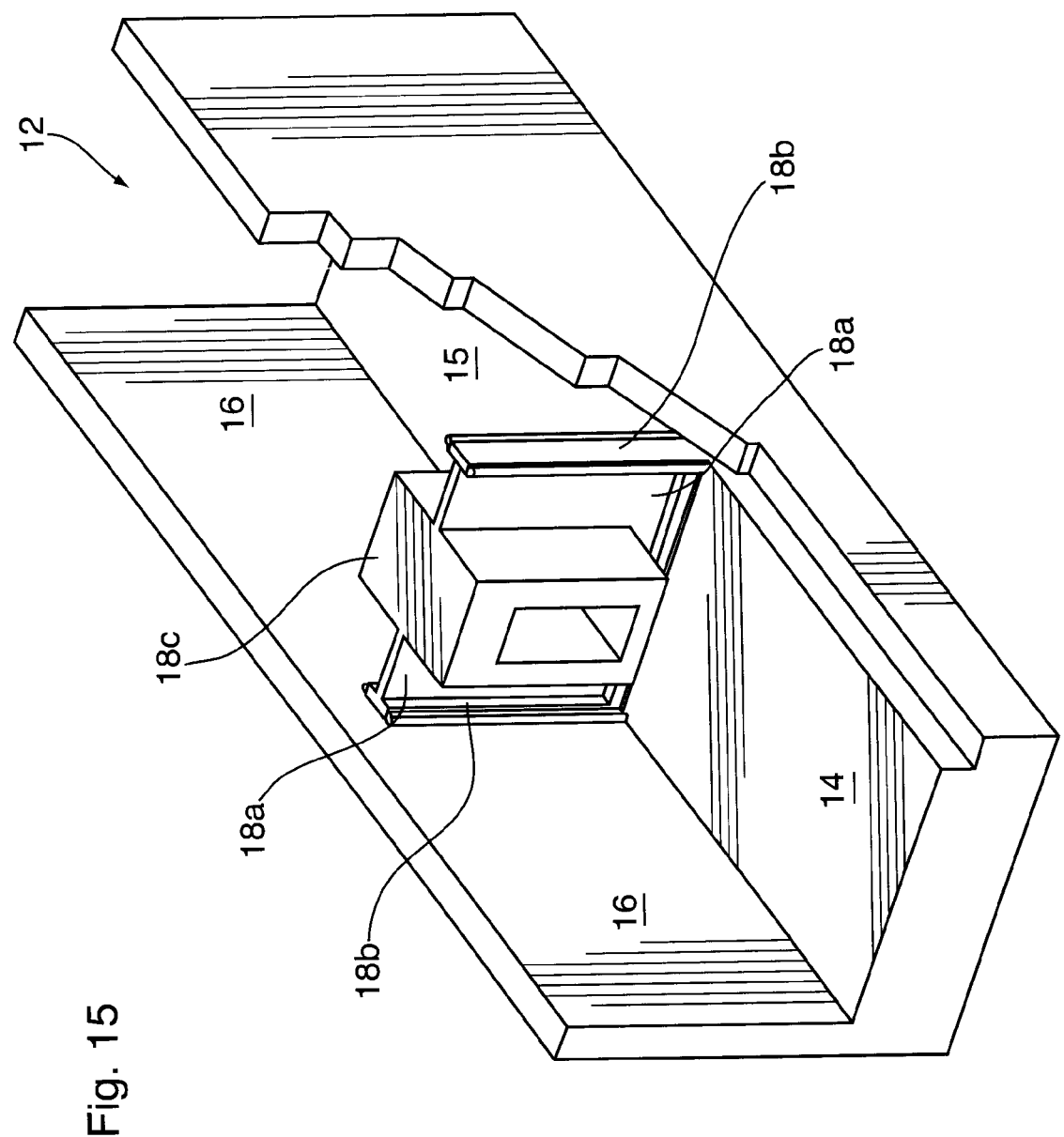

With reference to FIGS. 13-15, there is shown a modification of fluid treatment system 10 illustrative in FIG. 1. Specifically, bulkhead 18 in fluid treatment system 10 in FIG. 1 has been modified to include a prefabricated bulkhead U-shaped channel element 18a which is disposed in a channel to form element 18b attached to channel side walls 16 and channel floor 14. A bulkhead sub-unit element 18c is disposed in prefabricated bulkhead U-shaped channel element 18a.

In some installations, the use of such a prefabricated bulkhead system shown in FIGS. 13-15 may be more convenient and/or less costly than casting bulkhead element 18 shown in FIG. 1. The details of fluid treatment system 10 and radiation source module 100 are otherwise similar to those discussed above.

FIG. 15 illustrates a system without radiation source module 100 and the module removal device.

Figure 16:
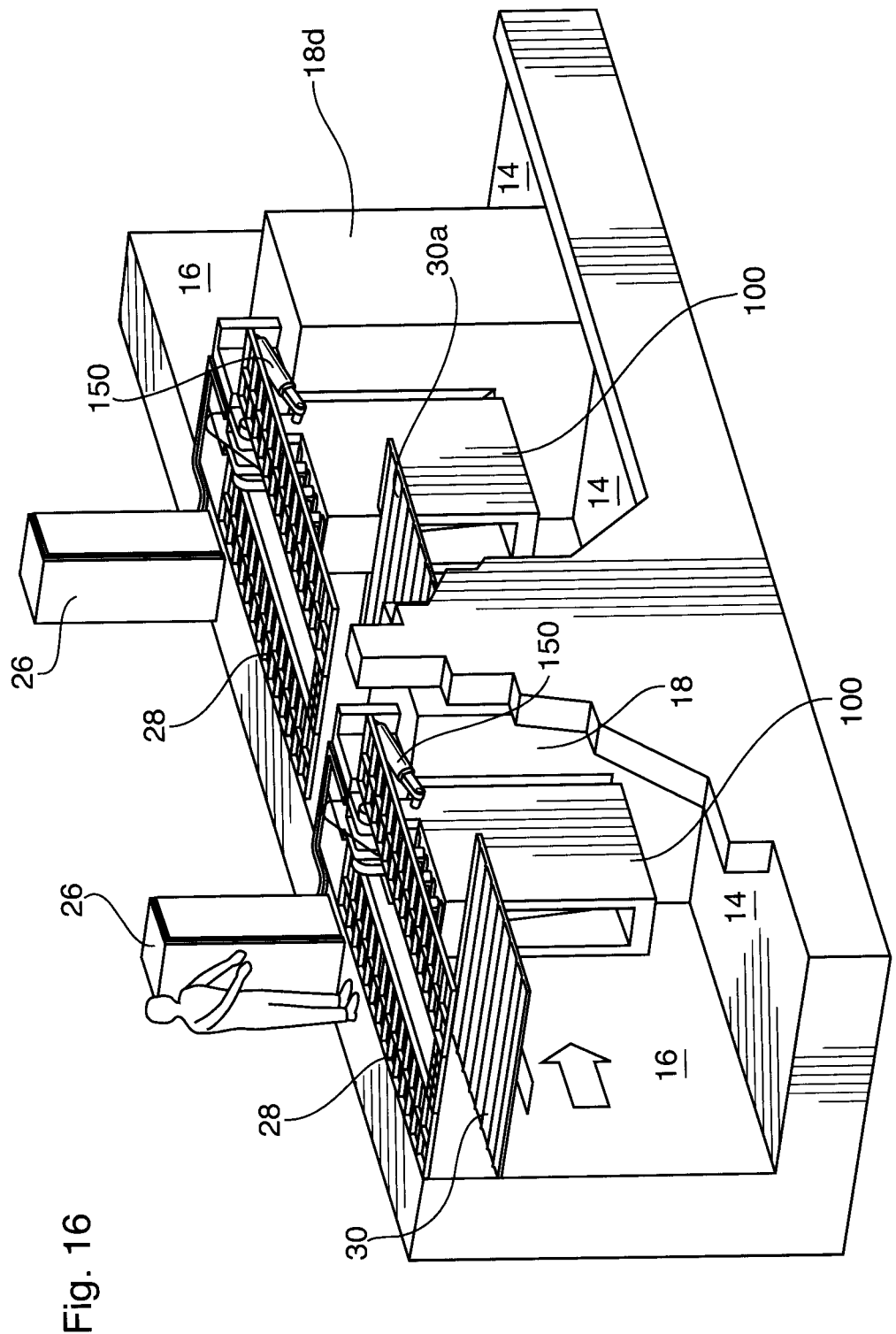
Figure 17:
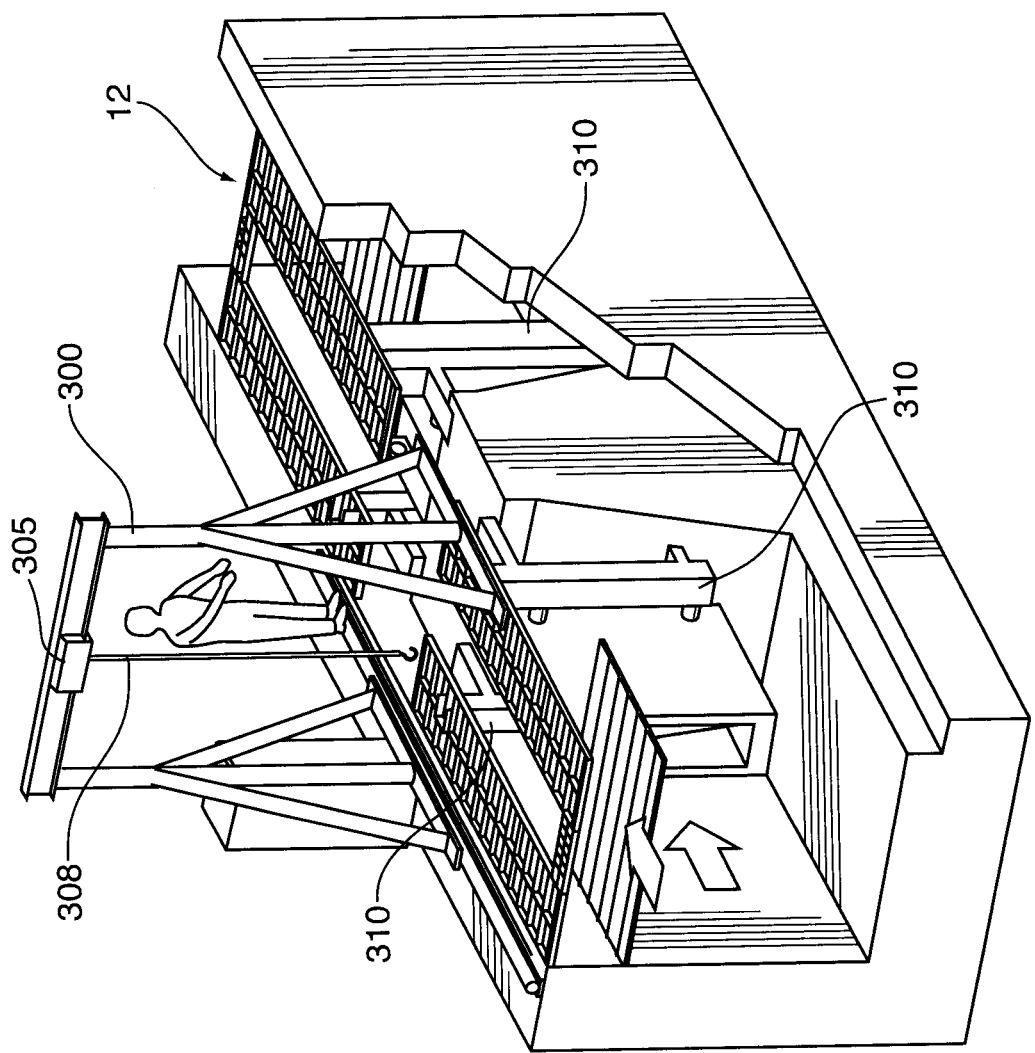

FIG. 16 illustrates a modification of fluid treatment system 10 shown in FIG. 1. Specifically, in FIG. 16, a second bulkhead 18d is disposed downstream of bulkhead 18 to provide for additional exposure of fluid in open channel 10 to radiation. Each of bulkheads 18,18d are combined with a radiation source module 100 disposed upstream thereof—i.e., there is no radiation source module facing and contacting the downstream portion of bulkheads 18,18d. All other details of fluid treatment system 10 and radiation source module 100 are similar to those described above.

With reference to FIGS. 17-21, there is illustrated a modification to fluid treatment system 100 illustrated in FIG. 1. Specifically, in FIGS. 17-21, the module removal device operates on the basis of linear translation instead of rotation. Thus, radiation source modules 100 are lifted in a relatively straight manner from open channel 12.

As shown, there is provided a module translation device 300 at the top of open channel 12. Module translation device 300 is movable along open channel 12 to move radiation source modules that are disposed upstream and downstream of bulkhead 18. Disposed in open channel 12 is a bulkhead guiderail 310. Module translation device 300 further comprises a winch 305 (or similar device) and a cable 308 for connection to radiation source module 100.

Figure 18:
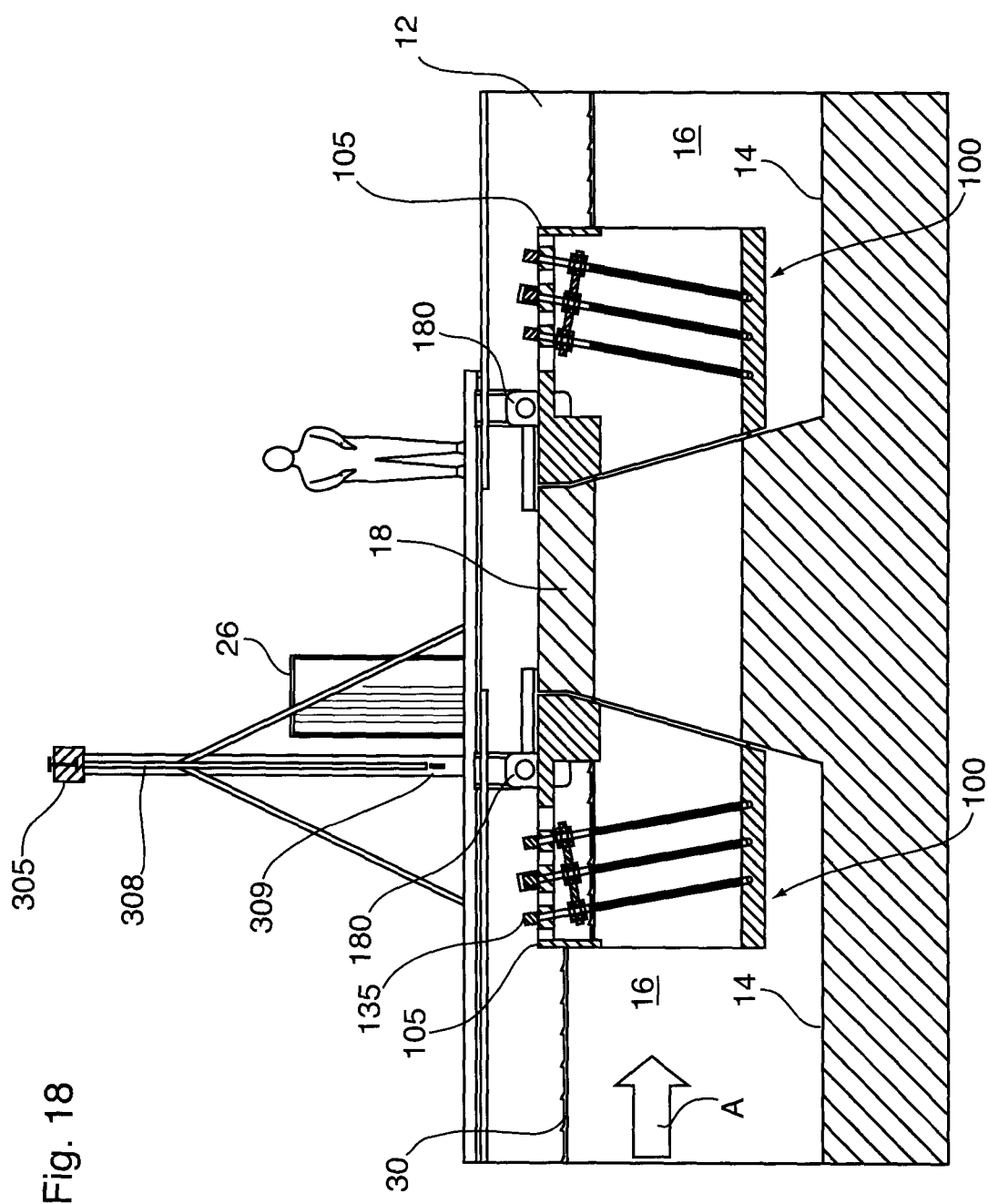
Figure 19:
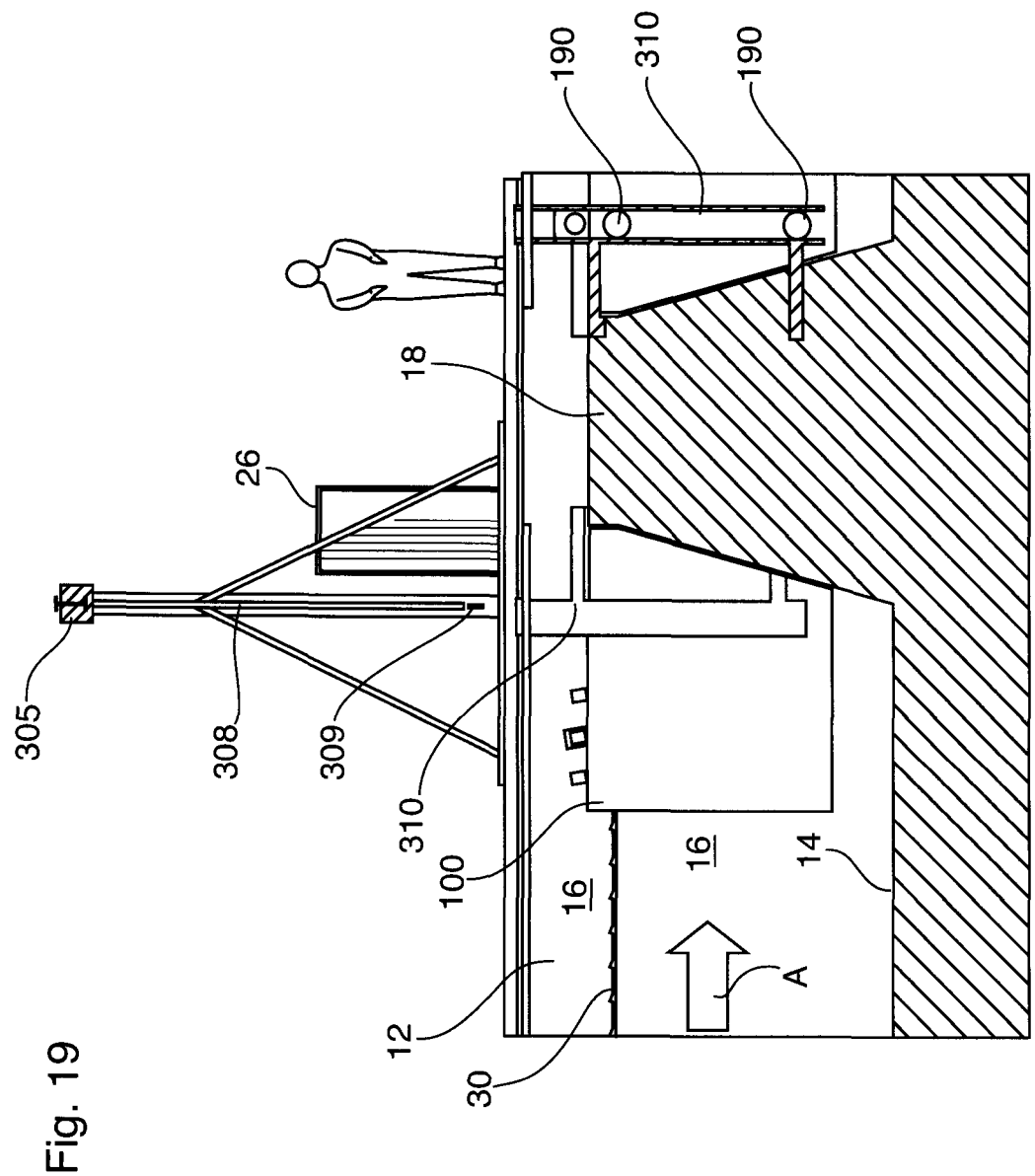

With particular reference to FIGS. 18-19, the shape of bulkhead 18 and housing 105 of radiation source module 100 have been modified to facilitate translation type movement of radiation source module 100 during extraction or installation thereof. In addition, radiation source module 100 has been modified to provide a module lifting eyelet 180 on top of housing 105. Radiation source module 100 has been further modified to include a roller 190 that is disposed within bulkhead guiderail 310.

Figure 20:
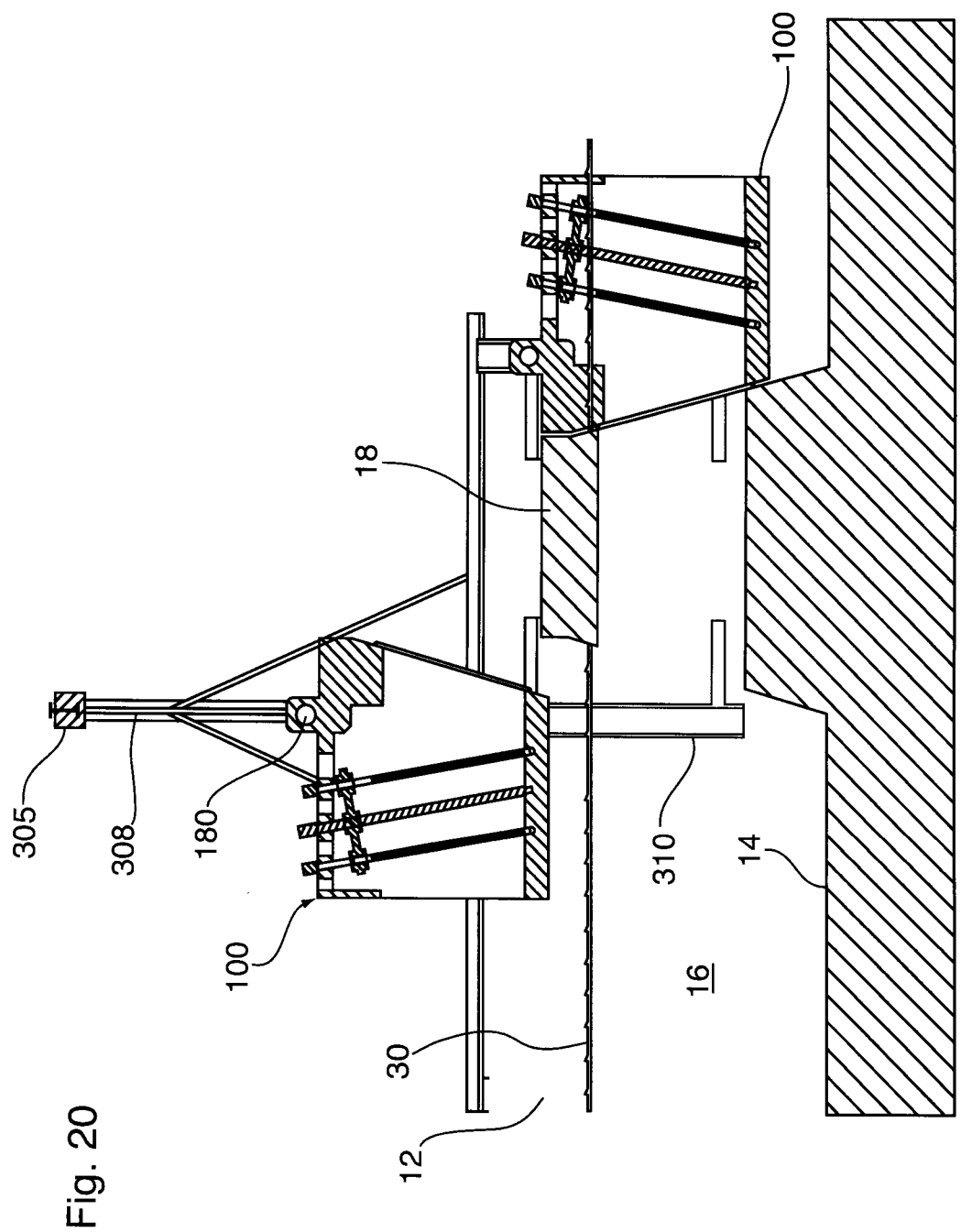
Figure 21:
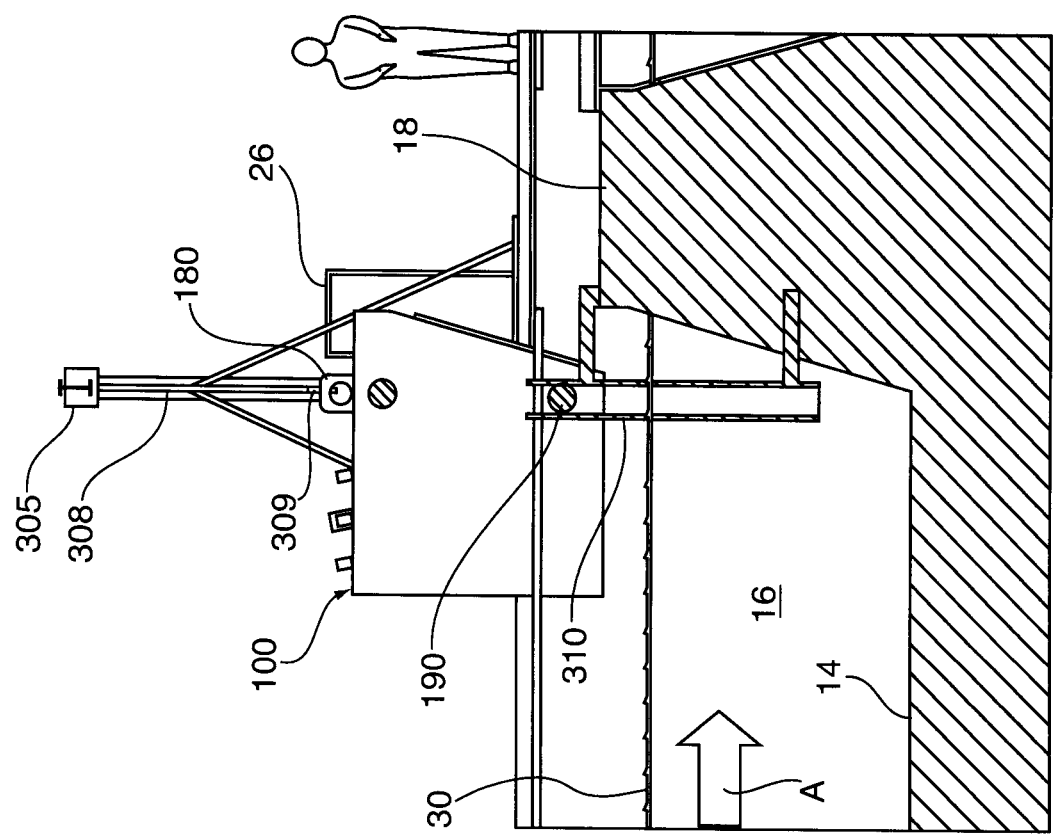

When it is desired to extract radiation source module 100 from open channel 12, a hook 309 at the end of cable 308 is engaged with eyelet portion 180 on radiation source module 100. Next, winch 305 is actuated to retract cable 308 thereby lifting the radiation source module 100 out of open channel 12. By providing roller 190 in bulkhead guiderail 310, inadvertent movement of radiation source module 100 during extraction can be obviated or mitigated. Extracted radiation source module 100 is shown in FIGS. 20-21.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. For example, while the motive element of module extraction device shown in the illustrated embodiments includes a mechanical device such as winch, it is possible to modify these embodiments so that the module extraction device is human powered It is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

What is claimed is:

1. A radiation source module for use in a fluid treatment system, the radiation source module comprising:
   a housing having an inlet, an outlet and a fluid treatment zone disposed between; the fluid treatment zone comprising a first wall surface and a second wall surface interconnected by a floor surface, the first wall surface, the second wall surface and the floor surface configured to receive a flow of fluid that is unconstrained at the upper surface thereof through the fluid treatment zone the upper surface of the fluid in the housing being above the inlet;
   a plurality of radiation source assemblies arranged as an array in the fluid treatment zone, each radiation source assembly being: (i) secured with respect to the first wall surface and the second wall surface, and (ii) configured to have a distal portion disposed in the flow of fluid and a proximal portion disposed outside of the flow of fluid; the array comprising at least two serially arranged rows of radiation source assemblies, each row comprising a plurality of radiation source assemblies; and
   a module motive coupling element connected to the housing and configured to be coupled to a module motive element to permit the radiation source module to be installed in and extracted from the fluid treatment system.

2. The radiation source module defined in claim 1, wherein the first wall surface comprises a plurality of first fluid deflector elements projecting into the fluid treatment zone.

3. The radiation source module defined in claim 2, wherein the plurality of first fluid deflector elements are in a spaced relationship along the first wall surface with respect to the direction of fluid flow through the fluid treatment zone.

4. The radiation source module defined in claim 1, wherein the second wall surface comprises a plurality of second fluid deflector elements projecting into the fluid treatment zone.

5. The radiation source module defined in claim 4, wherein the plurality of second fluid deflector elements are in a spaced relationship along the second wall surface with respect to the direction of fluid flow through the fluid treatment zone.

6. The radiation source module defined in claim 1, wherein the housing comprises a seal element configured to contact a surface of the fluid treatment system.

7. The radiation source module defined in claim 1, wherein the first wall surface and the second wall surface are substantially parallel to one another.

8. The radiation source module defined in claim 1, wherein the plurality of radiation source assemblies are configured such at a longitudinal axis thereof is arranged at an oblique angle with respect to the direction of fluid flow through the flow treatment system.

9. A fluid treatment system comprising:
an open channel for receiving a flow of fluid;
at least one radiation source module comprising:
a housing having an inlet, an outlet and a fluid treatment zone disposed between; the fluid treatment zone comprising a first wall surface and a second wall surface interconnected by a floor surface, the first wall surface, the second wall surface and the floor surface configured to receive a flow of fluid that is unconstrained at the upper surface thereof through the fluid treatment zone the upper surface of the fluid in the housing being above the inlet;
a plurality of radiation source assemblies arranged as an array in the fluid treatment zone, each radiation source assembly being: (i) secured with respect to the first wall surface and the second wall surface, and (ii) configured to have a distal portion disposed in the flow of fluid and a proximal portion disposed outside of the flow of fluid; the array comprising at least two serially arranged rows of radiation source assemblies, each row comprising a plurality of radiation source assemblies; and
a module motive element connected to the housing and configured to permit to be installed in and extracted from the fluid treatment system.

10. The fluid treatment system defined in claim 9, wherein the housing comprises a seal element configured to provide a substantially fluid tight seal between the housing a surface of the open channel.

11. The fluid treatment system defined in claim 9, wherein a bulkhead element is disposed in the open channel, the bulkhead element having an bulkhead inlet and a bulkhead outlet, the inlet of the housing configured to be disposed in fluid communication with the bulkhead outlet.

12. The fluid treatment system defined in claim 9, wherein a bulkhead element is disposed in the open channel, the bulkhead element having an bulkhead inlet and a bulkhead outlet, and a pair of radiation source modules are configured to be disposed in the open channel such that: (i) the outlet of the housing of a first radiation source module is configured to be disposed in fluid communication with the bulkhead inlet, and (ii) the inlet of the housing of a second radiation source module is configured to be disposed in fluid communication with the bulkhead outlet.

13. The fluid treatment system defined in claim 11, wherein the bulkhead element comprises a bulkhead seal configured to provide a substantially fluid tight seal between the bulkhead element and a surface of the radiation source module adjacent thereto.

14. The fluid treatment system defined in claim 9, further comprising a module motive element configured to be reversibly coupled to the module motive coupling element of the radiation source module.

15. The fluid treatment system defined in claim 14, wherein the module motive element is configured to rotate the radiation source module with respect to the open channel.

16. The fluid treatment system defined in claim 14, wherein the module motive element is configured to translate the radiation source module with respect to the open channel.

17. The fluid treatment system defined in claim 9, wherein the first wall surface is removable with respect to the housing.

18. The fluid treatment system defined in claim 9, wherein the second side wall surface is removable with respect to the housing.

19. The fluid treatment system defined in claim 9, wherein the first wall surface comprises a plurality of first fluid deflector elements projecting into the fluid treatment zone.

20. The fluid treatment system defined in claim 19, wherein the plurality of first fluid deflector elements are in a spaced relationship along the first wall surface with respect to the direction of fluid flow through the fluid treatment zone.

21. The fluid treatment system defined in claim 9, wherein the second wall surface comprises a plurality of second fluid deflector elements projecting into the fluid treatment zone.

22. The fluid treatment system defined in claim 21, wherein the plurality of second fluid deflector elements are in a spaced relationship along the second wall surface with respect to the direction of fluid flow through the fluid treatment zone.

23. The fluid treatment system defined in claim 9, wherein the plurality of radiation source assemblies are configured such at a longitudinal axis thereof is arranged at an oblique angle with respect to the direction of fluid flow through the flow treatment system.

24. The fluid treatment system defined in claim 9, wherein the module motive element is configured to linearly move the radiation source module with respect to the open channel.

25. A fluid treatment system comprising:
an open channel for receiving a flow of fluid;
at least one radiation source module comprising:
a housing having an inlet, an outlet and a fluid treatment zone disposed between; the fluid treatment zone comprising a first wall surface and a second wall surface interconnected by a floor surface, the first wall surface, the second wall surface and the floor surface configured to receive a flow of fluid that is unconstrained at the upper surface thereof through the fluid treatment zone the upper surface of the fluid in the housing being above the inlet;
a plurality of radiation source assemblies arranged as an array in the fluid treatment zone, each radiation source assembly being: (i) secured with respect to the first wall surface and the second wall surface, (ii) configured to have a distal portion disposed in the flow of fluid and a proximal portion disposed outside of the flow of fluid and (iii) configured such at a longitudinal axis thereof is arranged at an oblique angle with respect to the direction of fluid flow through the flow treatment system; the array comprising at least two serially arranged rows of radiation source assemblies, each row comprising a plurality of radiation source assemblies; and a module motive element connected to the housing and configured to linearly move the radiation source module with respect to the open channel.

\* \* \* \* \*